US006858436B2

(12) United States Patent
Zenhausern et al.

(10) Patent No.: US 6,858,436 B2
(45) Date of Patent: Feb. 22, 2005

(54) NEAR-FIELD TRANSFORM SPECTROSCOPY

(75) Inventors: Frederic Zenhausern, Fountain Hills, AZ (US); Chia-Fu Chou, Chandler, AZ (US)

(73) Assignee: Motorola, Inc., Schaumburg, IL (US)

( * ) Notice: Subject to any disclaimer, the term of this patent is extended or adjusted under 35 U.S.C. 154(b) by 234 days.

(21) Appl. No.: 10/135,790

(22) Filed: Apr. 30, 2002

(65) Prior Publication Data

US 2003/0203502 A1 Oct. 30, 2003

(51) Int. Cl.⁷ .............................................. G01N 21/00
(52) U.S. Cl. ....................... 436/164; 436/171; 250/306
(58) Field of Search ......................... 436/164, 171–172; 250/306–311

(56) References Cited

U.S. PATENT DOCUMENTS

| | | | |
|---|---|---|---|
| 5,018,865 | A | 5/1991 | Ferrell et al. |
| 5,538,898 | A | 7/1996 | Wickramasinghe et al. |
| 5,623,339 | A | 4/1997 | Wickramasinghe et al. |
| 5,624,845 | A | 4/1997 | Wickramasinghe et al. |
| 5,646,731 | A | 7/1997 | Wickramasinghe et al. |
| 6,052,238 | A | 4/2000 | Ebbesen et al. |
| 6,280,960 | B1 | 8/2001 | Carr |
| 6,621,079 | B1 * | 9/2003 | Shao et al. .................. 250/306 |
| 2002/0033952 | A1 | 3/2002 | Hill |
| 2002/0171837 | A1 * | 11/2002 | Cheng ......................... 356/436 |

FOREIGN PATENT DOCUMENTS

EP          0426571 A1      5/1991

OTHER PUBLICATIONS

Tegenfeldt et al. "Near–field scanner for moving molecules", Physical Review Letters, Feb. 12, 2001, v. 86, No. 7, pp. 1378–1381.*
Steinle et al. "Nfield thermal lens detector for gradient elution liquid chromatography" Analytica Chimica Acta, 1997, v. 353, pp. 207–213.*
Saiki et al. "Recent advances in near–field scanning optical microscopy", JSAP International, Jan. 2002, No. 5.*
Crabtree et al., "Shah convolution fourier transform detection," Analytical Chemistry, vol. 71, No. 11, Jun. 1, 1999, pp. 2130–2138.

* cited by examiner

*Primary Examiner*—Yelena G. Gakh

(57) ABSTRACT

An exemplary system and method for detecting at least one analyte in a sample comprises inter alia a source of radiation (300), a near-field aperture array (315), a chromatographic field (330), a detector (350), and a data processor (370). Disclosed features and specifications may be variously controlled, adapted or otherwise optionally modified to improve detection of any sub-diffraction-limited scale phenomena. Exemplary embodiments of the present invention representatively provide for improved S/N, increased sample throughput, refined spectral resolution and enhanced detection sensitivity.

40 Claims, 8 Drawing Sheets

NEAR-FIELD TRANSFORM SPECTROSCOPY

FIELD OF INVENTION

The present invention generally relates to spectroscopy and chromatography. More particularly, the present invention concerns a system and method for near-field transform detection of non-propagative evanescent phenomena.

BACKGROUND

The need to resolve objects smaller than those visible to the naked eye has existed from the beginning of observational science and natural philosophy. Since the $19^{th}$ Century, the fundamental limitations of employing visible light to realize enhanced optical resolution, while unwelcome, have generally been well understood. In practical terms, these limitations have typically involved the wavelength of light used, which generally defines the minimum scale of effective measurement this despite the best efforts of lens makers to perfect or otherwise improve the optical art. Consequently, conventional light-optical methods have increasingly resorted to smaller wavelengths with the trend in semiconductor fabrication, for example, being toward the deep ultraviolet in order to resolve sub-micron features below the diffraction limit of visible light. However, diffraction-imposed constraints are generally not unique to lithographic processes alone; analytical methods used in materials characterization studies (i.e., microscopies, polarization studies and various spectroscopic methods) also suffer from substantially similar limitations.

Near- and Far-fields

Near-field radiation ("NF"; also known as "evanescent radiation" or "forbidden light") comprises radiation that does not propagate through space, but rather is localized "near" the surface of objects, while far-field radiation ("FF"; also known as "normal radiation" or "allowed light") generally refers to propagative radiation. In general, all illuminated objects have both NF and FF components; however, most conventional spectroscopic methods generally avail themselves to diffraction-limited propagative components in the FF.

Near-field Microscopy

In 1928, Synge described but was not able to demonstrate sub-wavelength imaging using NF light. By 1972, Ash and Nicholls employed the NF for microwave microscopy. More recently, the development and subsequent implementation of Scanning Probe Microscopy (SPM), Scanning Tunneling Microscopy (STM) and Atomic Force Microscopy (AFM), as well as a variety of other methods, effectively set the stage for the application of the NF to optical techniques.

Scanning Near-Field Optical Microscopes (e.g., SNOM or NSOM) generally use sharp (e.g., sub-wavelength) probe tips in order to image at sub-wavelength optical resolution. See, for example, D. W. Pohl et al., "Optical Sthetoscopy Image Recording With Resolution $\frac{\lambda}{20}$",

*Appl Phys. Lett.* 44, 651–653, 1984. The, spatial resolution that may be achieved is generally defined by the size and shape of the probe tip. SPM also more generally includes a growing number of high resolution surface microscopy techniques (including NSOM) that use non-metrically sharp probe tips maintained very close to or even touching the sample surface and scanned in the xy plane of the sample using a combination of, for example, piezoelectric transducers, stepper motors and/or the like. See, for example, F. Zenhausern et al., "Scanning Interferometric Apertureless Microscopy: Optical Imaging at 10 Angstrom Resolution", *Science* 269, 1083–85, 1995; and U.S. Pat. No. 5,646,731 issued to Wickramasinghe et al. on Jul. 8, 1997.

Although NF light generally may not be used to directly image a sample, the interaction of NF light on a sample with a sharp sub-wavelength probe may be exploited to "scan" an image of the sample's surface. There are various approaches that have been used for this in the prior art. In one method, the sample is illuminated with FF light, either from the top surface (or, alternatively, with back-side illumination) which produces a NF on the top surface of a transparent sample. See, for example, F. Zenhausern et al., "Apertureless Near Field Optical Microscope", *Appl. Phys. Lett.*, 65(13), 1623, 1994. Introduction of a sharp sub-wavelength probe into the sample's NF scatters FF light from a surface area approximately equivalent to the terminal cross-sectional area of the probe tip. The scattered FF light propagates away from the probe site for subsequent detection by, for example, interferometric means. If the probe size is smaller than the wavelength of the light incident on the sample and the probe is xy scanned at a correspondingly fine scale over the sample surface, an image having finer resolution than the wavelength may be "built-up". If the probe is made with a tip having a terminal cross-sectional diameter on the order of about 100 nm and scanned at 100 nm intervals, in principle, 100 nm optical resolution may be achieved—much better than conventional FF light-optical techniques. See, for example, E. Betzig and J. K. Trautmais, *Science,* 257, 189, 1992.

In most cases, conventional FF mechanisms of optical contrast formation are generally applicable to NF imaging, however at much higher spatial resolutions—the ultimate limit of which is generally not believed to have yet been well characterized. Theoretically, it may be possible to construct atomically sharp NF probes to achieve atomic resolution. Other theories are based on the well-known $$\frac{2\pi}{\lambda}$$

spatial frequencies limits. In practical terms however, as the probe size decreases, the volume of NF light asymptotically decays to zero with a corresponding trade-off between resolution and sensitivity. Practical high-resolution NF microscopy methods thus require robust optical techniques as well as good probe designs.

Spectroscopy and Chromatography

In terms of spectroscopic applications, "imaging" (e.g., detection) systems in analytical chemistry and separation science, while generally diverse, embody near ubiquitous implementations of FF processes. FF spectrochemical techniques, such as absorbance, fluorescence and chemiluminescence methods, have been generally well known in the art with the vast majority of these methods adapted for single-point detection at or near the end of a chromatographic column. The separation mechanisms generally operate over a duration of time and length of column (e.g., chromatographic field) such that the sample is resolved into component analytes which may then be interrogated by a detector, usually at a fixed position in the column-flow based on, for example, the physical and/or chemical properties desired in order to yield an analyte signal recorded over the separation. The analyte output is thus collected in a chromatographic domain (e.g., "time domain"), such as the signal obtained, for example, in an electropherogram and/or the like. In other words, the chromatogram is a convolved reducible expression of the detection function F(d) (in most cases, a Dirac delta function δ) in combination with the separation function F(s).

Prior art spectroscopic methods have generally employed means for detecting small scale phenomena that typically involve the reduction of incident wavelength (DeBroglie or otherwise) in order to achieve enhanced spectroscopic resolution. While these approaches may be acceptable in certain FF (e.g., "radiatively propagative") systems, the broader application of chromatographic and spectroscopic technologies presents previously unresolved problems, for example, with respect to imaging below the diffraction limit of available FF methods. Accordingly, a representative limitation of the prior art concerns inter alia the effective and efficient NF detection of sub-diffraction-limited scale phenomena in, for example, a convolved G (F(d),F(s)) detection/separation domain.

SUMMARY OF THE INVENTION

In various representative aspects, the present invention provides a system and method for near-field spectroscopic interrogation of sub-diffraction-limited scale phenomena. In one exemplary aspect, a representative device comprising a source of radiation, a near-field aperture array, a chromatographic flow field, a detector and a data processor is disclosed. One advantage of the present invention includes the improvement of the signal-to-noise (e.g., S/N) ratio for spectroscopic measurements in order to achieve inter alia enhanced spectroscopic resolution. Additionally, the present invention also provides for increased sample throughput, with the utilization of multiplex detection and time-to-frequency transform methods, as well as single-molecule detection sensitivity. Other exemplary embodiments include detection systems and/or methods suitably adapted to employ apertureless NF generation.

In one representative aspect, a system is configured to transform time-domain signal input into frequency-domain output in order to achieve sub-diffraction-limited scale detection or imaging of analytes within a heterogeneous multi-component sample without requiring inter alia pre-conditioning of the initial starting conditions at the time of sample loading. Near-field transform spectroscopy also provides for a new regime of analyte-specific information by exploiting higher frequency information in the localized region of non-propagative evanescent fields.

The disclosed system and method may be readily adapted for parallel processing of samples and may be optionally implemented with cyclic chromatography to increase resolution in conjunction with faster separations. The disclosed system and method may also be optionally coupled with, for example, DNA micro-arrays and on-chip light sources. In one representative aspect, the present invention may further embody an integrated module for real-time monitoring and quantification of, for example: biomolecular reporters; chemical, luminescent, and/or magnetic tags, etc.; nucleic acid concentrations; PCR kinetics; flow-velocities; analyte mobilities and various epigenomic applications and/or the like.

Additional advantages of the present invention will be set forth in the Detailed Description which follows and may be obvious from the Detailed Description or may be learned by practice of exemplary embodiments of the invention. Still other advantages of the invention may be realized by means of any of the instrumentalities, methods or combinations particularly pointed out in the claims.

BRIEF DESCRIPTION OF THE DRAWINGS

Representative elements, operational features, applications and/or advantages of the present invention reside inter alia in the details of construction and operation as more fully hereafter depicted, described and claimed—reference being had to the accompanying drawings forming a part hereof, wherein like numerals refer to like parts throughout. Other elements, operational features, applications and/or advantages will become apparent to skilled artisans in light of certain exemplary embodiments recited in the detailed description, wherein:

Figure 1:
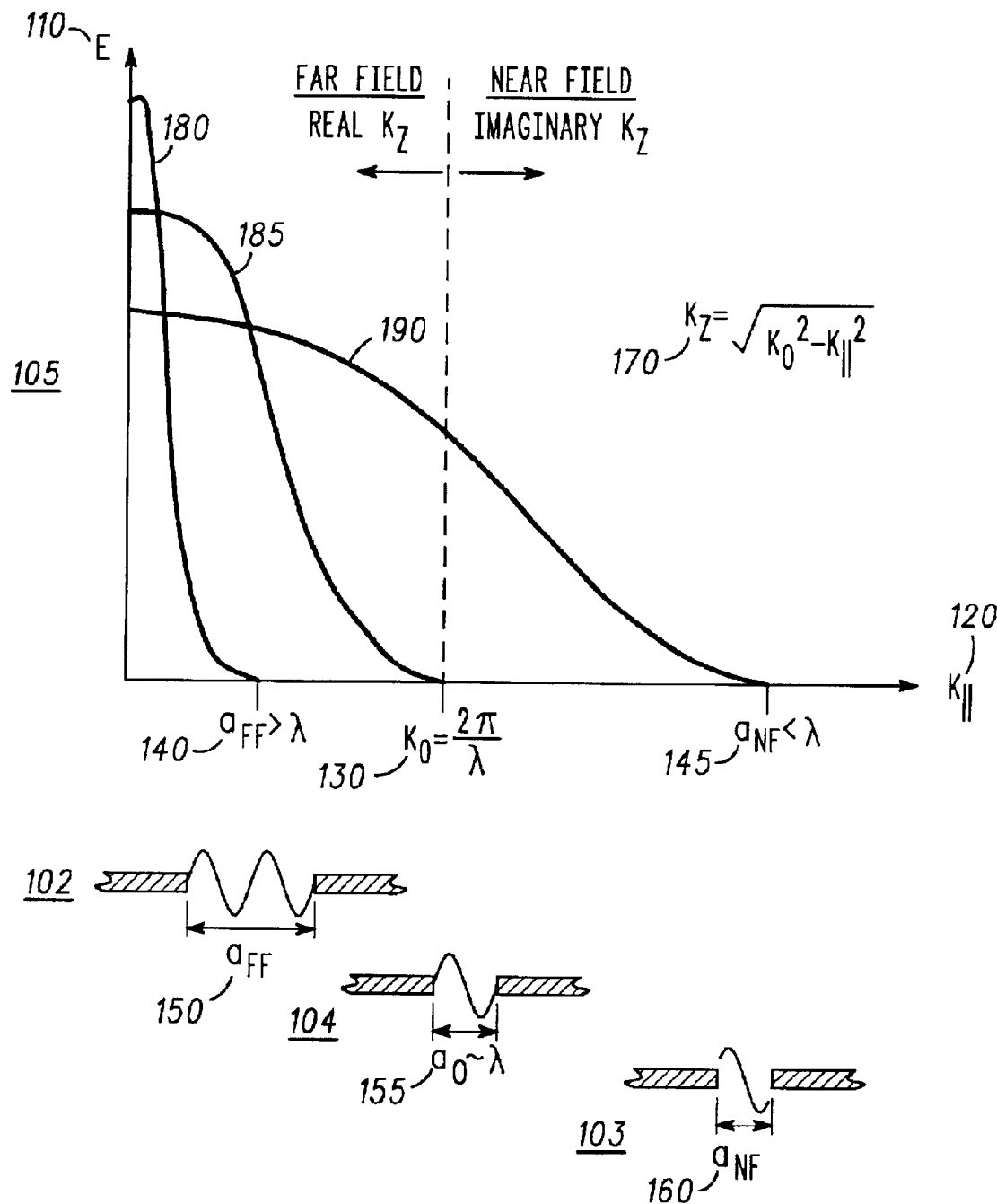
FIG. 1 illustrates representative ontology for near-field radiation as a function of aperture width in accordance with various exemplary embodiments of the present invention.

Those skilled in the art will appreciate that elements in the Figures are illustrated for simplicity and clarity and have not necessarily been drawn to scale. For example, the dimensions of some of the elements in the Figures may be exaggerated relative to other elements to help improve understanding of various embodiments of the present invention.

DETAILED DESCRIPTION OF EXEMPLARY EMBODIMENTS

The following descriptions are of exemplary embodiments of the invention and the inventors' conceptions of the best mode and are not intended to limit the scope, applicability or configuration of the invention in any way. Rather, the following description is intended to provide convenient illustrations for implementing various embodiments of the invention. As will become apparent, changes may be made in the function and/or arrangement of any of the elements described in the disclosed exemplary embodiments without departing from the spirit and scope of the invention.

Various representative implementations of the present invention may be applied to any system and/or method for NF measurement and/or de-convolution of sub-diffraction-limited scale phenomena. Certain representative implementations may include, for example: the improvement of S/N in a NF detection or imaging system; the improvement of sample-throughput in a NF separation, excitation and/or detection system; and single molecule sub-diffraction-limited scale excitation and/or detection. As used herein, the terms "near-field", "NF", "diffraction-limited", "small scale", "sub-diffraction-limited", "evanescent" and "forbidden light", or any variation or combination thereof, are generally intended to include anything that may be regarded as at least being susceptible to characterization as generally referring to: (1) radiation that does not propagate away from a sample, but rather is localized near the surface of the sample; (2) non-propagative radiation that oscillates in a localized vicinity near the surface of an object; (3) spatial constraints at least on the order of magnitude corresponding to the localized areas described in either of the immediately preceding elements (1) or (2) vide supra; (4) effective resolution on the order of magnitude corresponding to the localized areas described in either of the immediately preceding elements (1) or (2) supra; wherein said radiation comprises at least one of particle beam radiation, particle radiation (e.g., DeBroglie radiation), wave radiation, wave-packet radiation, electromagnetic radiation and/or any other radiative energy now known or hereafter derived or otherwise described by those skilled in the art. As used herein, the terms "radiative" and "propagative" are generally not used interchangeably, unless otherwise indicated. For example, "radiative" energy may be generally understood to comprise NF and FF components, whereas "propagative" energy may be generally understood as referring to FF radiation. On the other hand, as used herein, the terms "energy" and "radiation" may generally be used interchangeably and may also be understood to comprise matter-wave radiation in accordance with the DeBroglie wavelength $\lambda$ of a mass m traveling at a velocity v in accordance with the expression $$\lambda = \frac{h}{mv}.$$

As used herein, the terms "chromatography", and "separation", or any contextual or combinative referents or variants thereof, are generally intended to include any method, technique, process, apparatus, device or system suitably adapted to separate or otherwise process at least one sample comprising at least one analyte in order to inter alia produce or otherwise condition the spatial and/or temporal distribution of any component analyte and/or combination of analyte components in said sample. Additionally, as used herein, the terms "spectroscopy", "imaging", "interrogation" and "detection", or any contextual or combinative referents or variants thereof, are generally intended to include any method, technique, process, apparatus, device and/or system suitably adapted to read or otherwise process analyte-referent data in order to determine inter alia the presence and/or absence of any one analyte and/or any combination of analytes. Additionally, as used herein, the terms "transform" and "domain conversion", or any contextual or combinative referents or variants thereof, are generally intended to include any method, technique, process, apparatus, device and/or system suitably adapted to map a function $f(t)$ of data collected in t space into another function $g(\alpha)$ in $\alpha$-space.

A detailed description of an exemplary application, namely a system and method for chromatographic separation and spectroscopic Fourier detection of, for example, biomolecules using a NF aperture array, is provided as a specific enabling disclosure that may be generalized by skilled artisans to any application of the disclosed system and method for de-convolved measurement of sub-diffraction-limited scale phenomena in accordance with various embodiments of the present invention. Moreover, skilled artisans will appreciate that the principles of the present invention may be employed to ascertain and/or realize any number of other benefits associated with NF transform spectroscopy such as, but not limited to: improvement of signal averaging; improvement of S/N; reduced preparation and/or preconditioning of heterogeneous samples; improved sample loading; improvement in sample throughput; sample multiplexing and/or parallel sample processing; utilization of cyclic chromatography; faster analyte separation; integration with micro-array assay techniques and/or systems; improved detection sensitivity; access to new spectral information; increased resolution; real-time monitoring and/or analyte detection; particle velocimetry; microfluidic sample transport; single-molecule detection; mass data media storage; in situ monitoring of a chemical polishing process (i.e., CMP); and any other applications now known or hereafter developed or otherwise described in the art.

Diffraction Limit of Far-field Optical Resolution

FF optical systems employing lenses or mirrors are intrinsically limited in terms of spatial—resolution even with highly optimized designs. This limit is commonly known as the diffraction limit or "Abbé's limit", after the 19th Century optical researcher who first described the optical imaging process in terms of the diffraction of light waves. Abbé demonstrated that the smallest object or feature d that may be resolved by using a lens system is about half the wavelength of the light used $$d = \frac{0.61\lambda}{n\sin\theta},$$

wherein n is the refractive index of the medium between the sample and objective lens (i.e., ambient air corresponds to n=1.0), $\theta$ is the acceptance angle of the lens and n sin $\theta$ is the lens numerical aperture. Reducing the wavelength $\lambda$ (i.e., from red to blue) can improve the resolution, as can using oil/solid immersion lenses with larger indices of refraction (e.g., n>1.0). See, for example, S. M. Mansfield and G. S. Kino, *Appl. Phys. Lett.*, 57, 2615, 1990. It should be noted, however, that the actual experimental FF resolution is often lower than the theoretical diffraction limit due to inter alia aberrations caused by non-ideal optical elements.

In high-resolution microscopes, oil-immersion objectives with apertures of n sin$\theta$>1.4 are used, resulting in a theoretical maximum resolution of $d_{min} \geq 0.4\lambda$. This theoretical limit is termed the "Rayleigh criterion" and assumes the use of incoherent light. For coherent light, under, certain it circumstances, the resolution may be somewhat improved in accordance with $$d_{min} \approx 0.5 \frac{\lambda}{n\sin\theta}.$$

However, non-scanning coherent light microscopy is generally difficult since the images are often superimposed with diffraction patterns that originate from small structures in the optical path. Optimal resolutions may usually be obtained by scanning confocal microscopy where the image of an illuminating aperture in the sample plane coincides with a "back-focused" image of the exit aperture. Although the size of the illumination and detection spots are generally diffraction limited, the effective resolution obtained by the combination of the two is typically enhanced by a factor of about $\sqrt{2}$. For recording images of a sample, the illumination spot may be scanned, for example, by translating the sample. In addition to high lateral resolution, confocal FF microscopy also permits imaging of planes at varying depths within the sample.

Ontological Basis for Near-field Phenomena

The light field at the surface of an object typically contains more information (e.g., higher spatial frequencies) than may be imaged with conventional optical techniques. Spatial frequencies that reach the imaging lens (e.g., propagative low-frequency energy passing through the numerical aperture) may generally be "seen". However, higher spatial frequencies exist at the sample surface, but decay exponentially within a distance generally less than that of the incident wavelength. These high spatial frequencies are termed the "near-field" (NF); which is to say that the detector must be very near to the probe region in order to measure them. The process of low-frequency light propagating away from the sample surface generally filters out the fine near-field details.

The concept of using NF high spatial frequency light for imaging was first proposed by Synge in 1928. He suggested that by combining a sub-wavelength aperture to illuminate an object together with a detector very close to a sample (e.g., <<$\lambda$; "in the near-field"), high resolution could be achieved below the Abbé diffraction limit. In general, an object in-line between the aperture and detector may be imaged in the near-field, whereas other distant objects typically are not. It was over forty years until Ash and Nicholls subsequently described a microwave imaging technique using NF optics, thereby setting the stage for the development of SPM methods in the 1980's to bring NF optical microscopy to practical application. See, for example, E. Betzig et al., *Appl. Phys. Lett.*, 51, 2088, 1987; and F. Zenhausern, et al., *Appl. Phys. Lett.*, 65,1623–25, 1994.

Another approach is to increase the numerical aperture above the limit of which is obtainable in air. This has been demonstrated by using evanescent fields from internally reflected light. See, for example, J. M. Guerra, "Photon Tunneling Microscope", *App. Opt.*, 29, 3741–52, 1990; S. M. Mansfield et al., *Opt. Lett.*, 18, 305, 1993. Both of these configurations general provide definition that is reduced by a factor of $$\frac{1}{n}$$

from that of a standard confocal microscope. For example, with an objective having a numerical aperture of 0.8, the effective numerical aperture would be 1.6 for n=2 (i.e., for solid immersion lenses) and the theoretical half-power width of a confocal microscope would accordingly be $$\frac{0.37\lambda}{n\sin\theta}$$

(where n sin θ again is the numerical aperture) corresponding to about 93 nm for a wavelength $\lambda$=405 nm.

In the far-field (FF) regime, light waves propagate in a direction normal to the sample surface or through an aperture larger than the wavelength for detection at a distance >>$\lambda$. FF light comprises wave vectors $k_z$ with real components in the propagation direction z, called homogeneous waves or "allowed" light. The graph 105 in FIG. 1 illustrates the relationship between the parallel wavenumber vectors $k_{81}$ 120 and the field strength E 110; with the wavelength/aperture in reciprocal units $$\frac{1}{\lambda}$$

(increasing from left to right on the abscissa).

Figure 2:
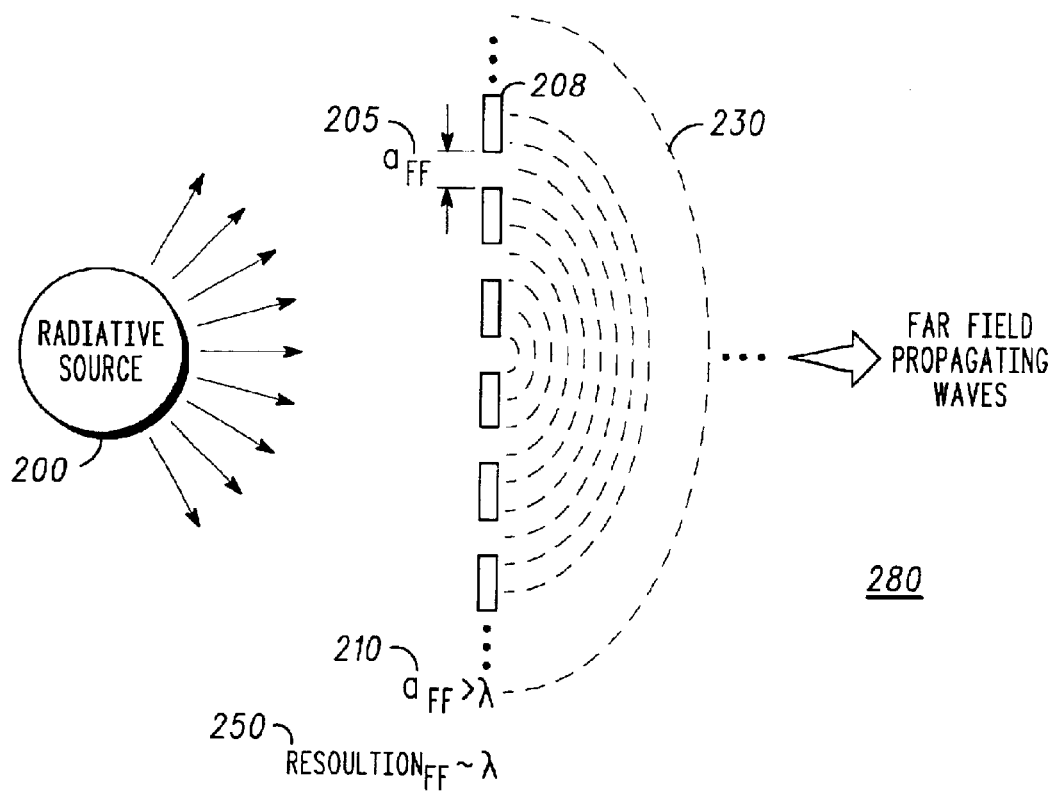
FIG. 2 illustrates representative ontology for near-field wave evolution as a function of aperture width in accordance with various exemplary embodiments of the present invention.
Figure 2:
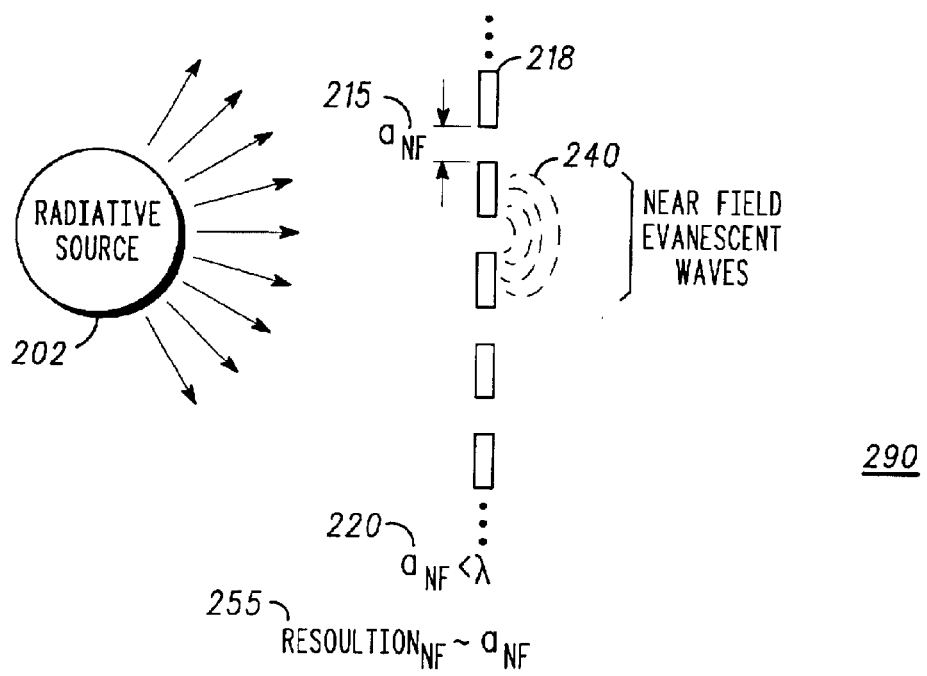

FF radiation generally refers to propagative radiation 230 as illustrated, for, example, in FIG. 2. In the FF system 280, an aperture grating 208 is exposed to a source of radiant energy 200 wherein the grating's aperture width $a_{FF}$ 205 is generally larger than the incident wavelength $\lambda$ 210. The resulting energy pattern 230 that develops on the opposing surface of the grating 208 propagates away from the grating in what is termed the "far-field". The effective FF resolution 250 is typically on the order of magnitude of the wavelength $\lambda$. Accordingly, in FF processes, the wavelength $\lambda$ generally defines the minimum resolvable spatial resolution (e.g., the diffraction limit of optical and spectroscopic resolution).

NF radiation, on the other hand, comprises radiation 240 that does not propagate through space, but rather is localized "near" the surface of objects. For example, in the NF system 290 depicted in FIG. 2, a NF aperture grating 218 is exposed to a source of radiant energy 202 wherein the grating's aperture width $a_{NF}$ 215 is generally smaller than the incident wavelength $\lambda$ 220. The resulting energy pattern 240 that emerges on the opposing surface of the grating 218 is localized to a relatively small area in which the energy oscillates back and forth in what is referred to as the "near-field". Accordingly, the effective resolution 255 in the NF regime typically corresponds to the order of magnitude of the near-field aperture $a_{NF}$ 215.

NF light has wave vectors with imaginary $k_z$ components 170 perpendicular to the apertures 102, 103 and 104 which do not propagate in that direction, but may still propagate parallel to it. The waves decay in the parallel direction within a short space, e.g., less than the wavelength $\lambda$, and are accordingly called "evanescent" or "forbidden". Detecting them requires working in this small "near-field region" near the sample.

The relative volume of available NF light, as compared to FF light, generally requires sensitive detectors and efficient instrument designs when conducting measurements in the NF. For example, the volume of FF light traveling through a large aperture 150 is generally much larger than the NF light that travels through a sub-wavelength aperture 160: notice the area under the curve 190 (e.g., the profile for a NF aperture $a_{NF}$ 160) as compared to the area under the curve 185 (e.g., the profile for an aperture $a_0$ 155 having dimensions on the order of the wavelength $\lambda$) and the area under the curve 180 (e.g., the profile for a FF aperture $a_{FF}$ 150); all to the right of $k_0$ 130, corresponding to the imaginary components of $k_z$ 170 in the NF.

Physically constrained light involved in the imaging and/or detection of sample features smaller than $\lambda$ (e.g., at a sharp probe tip or through a sub-wavelength aperture) generally comprises a spectrum of waves with wavenumber vectors (e.g., spatial frequencies) smaller in real space than the wavelength or aperture elements themselves. However, unless the detector is placed very close to the NF region, these features will be "lost" since NF light does not propagate away from this region. The $k_0$ "cut-off" 130 (corresponding to an aperture dimension $a_0$ 155 on the order of the wavelength $\lambda$ as shown, for example, in 104) is generally not distinct due to the overlap between the FF and NF regions. Qualitatively, however, the NF may be said to comprise the regime of "less than a wavelength" 145 while the FF generally corresponds to the regime of "more than a wavelength" 140.

The appearance of sub-diffraction limited localized oscillations of high spatial frequencies (e.g., NF phenomena) are generally not limited to applications employing only visible light. Any energy emission, whether in the form of field fluctuations or localized matter-wave packets having finite, non-zero momentum (i.e., DeBroglie matter waves) may be shown to demonstrate propagating FF components that carry energy away from the source/sample as well as asymptotically decaying NF evanescent components confined to the close vicinity of the source/sample. Indeed, any energy transport process may be used to produce localized near-fields, to include, but not limited to: electromagnetic radiation, monochromatic radiation, polychromatic radiation, polarized radiation, circularly-polarized radiation, coherent radiation, incoherent radiation, particle beams, visible light, ultraviolet light, infrared light, radio waves, microwaves, x-rays, gamma-rays and such other energy transport processes (generally termed "radiation") now known or hereafter derived or otherwise described by those skilled in the art.

As a representative example, the electromagnetic field of an oscillating electric dipole, with the dipole axis parallel to the z direction, may be considered. The dipole located at a position $\vec{r}_0$ is characterized by an electric polarization $\vec{P}(\vec{r},t)=p(t)\delta(\vec{r}-\vec{r}_0)\vec{n}$ where p(t) refers to the time-dependent amplitude and $\vec{n}$ is a normalized direction vector; here, $$\vec{n} = \begin{pmatrix} 0 \\ 0 \\ 1 \end{pmatrix}.$$

In polar coordinates, the solution of Maxwell's equations for this representative system are, for example:

$$E_R = 2\left(\frac{[p]}{R^3} + \frac{[\dot{p}]}{cR^2}\right)\cos\theta$$

$$E_\theta = \left(\frac{[p]}{R^3} + \frac{[\dot{p}]}{cR^2} + \frac{[\ddot{p}]}{c^2R}\right)\sin\theta$$

$$H_\phi = \left(\frac{[\dot{p}]}{cR^2} + \frac{[\ddot{p}]}{c^2R}\right)\sin\theta$$

where $[p] = p\left(t - \frac{R}{c}\right)$ is the retarded value of the time-dependent amplitude, c is the speed of light, $E_R$ is the electric field along the R coordinate, $E_\theta$ is the electric field along the θ coordinate, and $H_\phi$ is the magnetic field along the φ coordinate. Two regions may accordingly be distinguished: the FF region where $$R \gg \frac{\lambda}{2\pi}$$

(with $$\lambda = c\frac{2\pi}{\omega}$$

representing the optical wavelength corresponding to the oscillation frequency ω), and the NF region of the dipole where $$R \ll \frac{\lambda}{2\pi}.$$

For the FF region, the $$\frac{1}{R^2} \text{ and } \frac{1}{R^3}$$

terms may be neglected to the extent that they are generally dominated by the $$\frac{1}{R}$$

contribution. The resulting expression corresponds to the well-known dipole-radiation field (e.g., the FF):

$$E_R = 0$$

$$E_\theta = \frac{[\ddot{p}]}{c^2R}\sin\theta$$

$$H_\phi = \frac{[\ddot{p}]}{c^2R}\sin\theta$$

Since the FF decays as $$\frac{1}{R},$$

energy is observed to emanate (e.g., propagate) away from the dipole. This can be demonstrated by taking the integral of the Poynting vector $$\vec{S} = \frac{c}{4\pi}\vec{E} \times \vec{H} \propto \frac{1}{R^2},$$

representing the rate at which energy flows through a unit surface area perpendicular to the flow vector, over the surface of a sphere of radius R. The resulting expression may be shown to be finite and independent of R. However, one of the characteristics of propagative dipole radiation is that generally no emanations occur along the dipole axis:

$$E|_{\theta=0} = 0 \text{ for } R \gg \frac{\lambda}{2\pi}.$$

For the $$R \ll \frac{\lambda}{2\pi}$$

region of the dipole, the $R^2$ and $R^3$ terms dominate, representing the NF high spatial frequencies. Accordingly, it is relatively straightforward to demonstrate that the corresponding surface integral of the NF Poynting vector over a sphere of radius R vanishes in the limit of R→∞. Of particular interest is that this integral does not vanish at finite radius, which means that non-propagative energy transport, in fact, does take place. However, since none of the high spatial frequency energy propagatively emanates from the source, the NF energy oscillates back and forth within a region termed the "NF zone". It is also of interest to note that unlike the FF, the NF does not vanish along the dipole axis.

For relatively large objects comprising many coherently radiating dipoles, the resulting electromagnetic fields may be much more complicated to calculate. Light propagation behind objects (i.e., apertures, gratings, etc.) that are illuminated by a coherent source is often described by scalar diffraction theory (e.g., Fourier optics). Here, the scalar amplitude of the electric and magnetic fields are treated and the vectorial nature of the electromagnetic field is generally neglected.

For large distances (e.g., in the FF) and objects that are large compared to the wavelength of incident radiation, Fourier optics yields reasonably accurate results in agreement with experiment. In the NF zone of small objects, however, strong cross coupling of vector components occurs; i.e., for a single dipole, the radial vector components in the NF vanish with large distances and scalar Fourier optics does not apply.

Nevertheless, the existence of evanescent waves in the NF may be generally modeled, at least qualitatively, by scalar Fourier optic theory. For example, given the amplitude of the electromagnetic field U within a certain plane (i.e., the surface of a flat object), the field U may be expanded into Cartesian plane waves by, for example, Fourier transformation:

$$U(x, y, z=0) = \frac{1}{\sqrt{2\pi}} \int\int dk_x dk_y A(k_x, k_y; z=0) e^{i(k_x x + k_y y)}$$

wherein $A(k_x, k_y)$ is called the angular spectrum. The propagation of the field along z is given by the scalar wave equation $\Delta U + k^2 U = 0$ with $$k = \frac{2\pi}{\lambda}.$$

By applying the scalar wave equation to the plane wave equation, the propagation of the angular spectrum may be obtained as:

$$A(k_x, k_y; z) = A_0(k_x, k_y) e^{iz\sqrt{k^2 - k_x^2 - k_y^2}}$$

wherein $A_0(k_x, k_y) = A(k_x, k_y; z=0)$. Combining the propagation of the angular spectrum with the plane wave equation yields:

$$U(x, y, z) = \frac{1}{\sqrt{2\pi}} \int\int dk_x dk_y A_0(k_x, k_y) e^{i\vec{k}\cdot\vec{r}} \text{ with } \vec{k} = \begin{pmatrix} k_x \\ k_y \\ \sqrt{k^2 - k_x^2 - k_y^2} \end{pmatrix}.$$

Thus, U may be considered as a superposition of three-dimensional plane waves with the amplitude of the scalar wave vectors $$|\vec{k}| = k = \frac{2\pi}{\lambda}.$$

For z→∞ (e.g., the Fraunhofer diffraction limit), the following well-known expression may be obtained:

$$U(x, y, z \to \infty) = \frac{1}{\sqrt{2\pi}} A_0\left(k\frac{x}{z}, k\frac{y}{z}\right).$$

The resulting diffraction pattern, at large distance, corresponds to the Fourier transformation of the field distribution within the object plane z=0. However, since the maximum value for $k_{\parallel} = \sqrt{k_x^2 + k_y^2}$ corresponds to $k_{\parallel}^{max} = k$, not all Fourier components may actually be mapped. Fourier components with larger $k_{\parallel}$ values decay in the limit of z→∞ according to $$A(k_{\parallel}; z) = A_0 k_{\parallel} e^{-z\sqrt{k_{\parallel}^2 - k^2}}$$

for $k_{\parallel} > k$.

These components may be regarded as qualitative metrics of the NF comprising information of sub-wavelength structures in the object plane. By measuring the field distribution at z>>λ, it may be observed that the information about these structures is, in fact, lost. A direct consequence of this result is the Rayleigh criterion for the lateral resolution of a FF microscope $$d_{min} = 0.61\frac{\lambda}{n\sin\theta},$$

where the diffraction limit $d_{min}$ is related to the wavelength of light λ and the numerical aperture n sin θ. Accordingly, it may be seen that information concerning sub-wavelength structures may be effectively obtained by measuring the radiation field distribution in the NF zone.

The preceding examples may prompt the question: "Why would the resolving power of an optical microscope be limited, even if all the light were collected with an infinitely large lens (e.g., sin θ=1)?" One answer may be that a lens generally operates to collect only FF components of the radiation (i.e., propagating light emitted by the object). This may be illustrated, for example, with a simple Gedanken experiment:

Given an infinitely extended grating with slit spacings d<λ equally illuminated by coherent light under normal incidence, the light-intensity distribution on a screen at distance l>>λ behind the grating would be generally observed to have a uniform intensity distribution. This is because the Bragg diffraction condition d sin θ=nλ is only fulfilled for the zeroeth-order diffraction peak. Thus, the information on the grating is lost in the FF and consequently, the grating cannot be recovered in the imaging plane of a FF microscope. However, if the screen or a small detector is moved close to the grating (e.g., l<<λ), there will be high intensity at the slit positions and low intensity in between. The NF light distribution therefore exhibits a strong distance dependence.

In principle, there generally is no resolution limit for NF microscopy; indeed, very high experimental resolutions of as little as 1 nm for visible light have been demonstrated. In most studies, a limitation of the lateral resolution of $$> \frac{\lambda}{10}$$

results from an experimental limit for effectively detectable light intensity.

Chromatography

In general, the majority of chemical analysis techniques are at best selective; few, if any, are actually specific. Consequently, the separation of analyte(s) from heterogeneous multi-component samples is often an important step in many analytical procedures. The most widely used conventional means of performing analytical separations are electrophoresis and chromatography—both comprising methods that find application in nearly every scientific discipline.

Column chromatography was invented and named by the Russian botanist Mikhail Tswett shortly after the turn of the $20^{th}$ Century. Tswett employed the technique to separate various plant pigments (i.e., chlorophylls and xanthophylls) by passing solutions of samples through a glass column packed with finely divided calcium carbonate. The separated solutes appeared as colored bands on the column, which accounts for the name Tswett gave for the technique from the Greek chroma meaning "color" and graphein meaning "to write".

Various chromatographic technologies have appeared in the last five decades, due not only to the development of several new types of methods but also to the growing need by engineers and scientists for better means for characterizing complex mixtures. The significant impact of these technologies may be demonstrated by the 1952 Nobel Prize awarded to Martin and Synge for their discoveries in the field of chromatography. Perhaps even more impressive is twelve Nobel Prize awards between the years of 1937 and 1972 that were based upon work substantially relying on various chromatographic techniques.

In general, chromatography comprises a diverse and important group of methods that permit separation of analyte components of complex mixtures, where many of these separations may be impossible or otherwise prohibitively difficult by other means. Typically, sample is dissolved in a mobile phase, which may be a gas, a liquid or a supercritical fluid. The mobile phase is then forced through an immiscible stationary phase, which is fixed in place in either a column or on a solid surface. The two phases are chosen so that the components of the sample distribute themselves between the mobile and stationary phases to varying degrees. Those analyte components that are strongly retained by the stationary phase move slowly with respect to the flow of mobile phase. In contrast, analyte components that are weakly held by the stationary phase travel more rapidly. As a consequence of these differences in flow velocities (e.g., mobilities), analyte components separate into discrete bands that may be analyzed qualitatively and/or quantitatively. See, for example, E. Heftmann, *Chromatography: Fundamentals and Applications of Chromatography and Electrophotometric Methods,* 1983; P. Sewell and B. Clarke, *Chromatographic Separations,* 1988; J. A. Jonsson, *Chromatographic Theory and Basic Principles,* 1987; R. M. Smith, *Gas and Liquid Chromatography in Analytical Chemistry,* 1988; E. Katz, *Quantitative Analysis Using Chromatographic Techniques,* 1987; and J. C. Giddings, *Unified Separation Science,* 1991. In general, chromatography is typically divided into five broad categories based on the mechanism of interaction between solute analytes and the stationary phase of the chromatographic field: adsorption chromatography; partition chromatography; ion-exchange chromatography; molecular exclusion chromatography; and affinity chromatography.

Adsorption chromatography is generally regarded as the oldest form of chromatography and makes use of a solid stationary phase with a liquid or gaseous mobile phase. Solutes are usually adsorbed onto the surface of stationary phase particles, while equilibration between the stationary phase and the mobile phase accounts for separation of solute analytes.

Partition chromatography involves a liquid stationary phase formed on a thin film on the surface of a solid support. Solute equilibrates between the stationary liquid and the mobile phase. In adsorption and partition chromatography, a substantially continuous equilibration of solute between the mobile and stationary phases occurs. Columns may be packed with stationary phase or may be open tubular with stationary phase coated on the inner walls.

Ion-exchange chromatography utilizes anions (i.e., $SO_3^-$) or cations (i.e., $N(CH_3)_3^+$) that are covalently attached to the solid stationary phase (i.e., usually a resin) and the mobile phase is typically a liquid. Analyte solute ions of opposite charge are attracted to the stationary phase by coulombic forces.

Molecular exclusion chromatography (e.g., gel filtration -or- gel permeation chromatography) separates molecules by size, with larger analyte solutes passing through the chromatographic field more quickly than smaller ones. Unlike other forms of chromatography, there is generally no attractive interaction between the stationary phase and the analyte solute; rather, the liquid or gaseous mobile phase passes through a porous gel. The pores are generally small enough to exclude larger molecules, but not smaller ones. Smaller molecules usually take longer to pass through the column because they enter the gel pores and therefore must flow through a larger volume before leaving the column. In molecular exclusion chromatography, the fraction of stationary-phase volume available to solute generally decreases as the size of the solute molecules increase.

Affinity chromatography is generally believed to be the most selective type of chromatography—employing specific interactions between one kind of analyte molecule and a second covalently attached (e.g., immobilized) to the stationary phase. For example, the immobilized molecule may be an antibody to a particular protein. When a mixture containing, for example, several hundred proteins is passed through the chromatographic field, only the specific protein that reacts with the corresponding antibody will generally be bound to the column. After washing the remaining solutes from the column, the desired protein may thereafter be dislodged, for example, by changing the pH or ionic strength. Affinity chromatography generally relies on chemically specific, non-covalent interactions between the stationary phase and at least one analyte solute in a heterogeneous sample.

The speed of the mobile phase passing through a chromatographic field is expressed either as a volume flow rate or as a linear flow rate. Consider, for example, a liquid chromatography experiment in which the column has an inner diameter of 0.60 cm (radius r=0.30 cm) and the mobile phase occupies 20% of the column volume. Each centimeter of column length l has a volume corresponding to $\pi r^2 \times l$; here 0.283 mL, of which 20% (e.g., 0.0565 mL) accounts for the mobile phase (e.g., the solvent system). The volume flow rate (i.e., $\frac{mL}{min}$)

expresses how much volume of solvent per unit time travels through the chromatographic field. The linear flow rate (i.e., $\frac{cm}{min}$)

tells how many unit distances of column length are traveled per unit time by the solvent system. In the instant example, because 1 cm of column length contains 0.0565 mL of mobile phase, 0.3 mL would occupy $$\frac{0.3 \text{ mL}}{0.0565 \frac{mL}{cm}} = 5.3 \text{ cm}$$

of column length. Accordingly, the linear flow rate corresponding to $0.3 \frac{mL}{min}$ is $5.3 \frac{cm}{min}$.

Analytes eluting from a chromatographic field may be observed with a variety of detectors, such as, for example: thermal conductivity detectors; flame ionization detectors; electron capture detectors; flame photometric detectors; alkali flame detectors; sulfur chemiluminescence detectors; atomic emission detectors and the like. The trace of the detector response as a function of elution time is known as a chromatogram. The retention time $t_r$ for each component is the time needed after injection of the sample onto the chromatographic field until the corresponding analyte is detected. Unretained mobile phase travels through the column in a minimum time $t_m$. The adjusted retention time $t'_r$ for a solute is the additional time required for analyte to travel the linear transport distance of the chromatographic field, beyond the time required by unretained solvent in accordance with $t'_r = t_r - t_m$.

The relative retention of two components is given as a quotient of the corresponding adjusted retention times. The capacity factor for a single component is the adjusted retention time divided by the elution time for the solvent. Capacity factor generally describes the ratio of time spent by solute in the stationary phase to time spent in the mobile phase. When scaling up from a small sample load to a large load, the cross-sectional area of the column is typically increased in proportion to the sample load while column length and linear flow rate are generally held constant.

For any two components 1 and 2, the relative retention α is defined as $$\alpha = \frac{t'_{r2}}{t'_{r1}}$$

where $t'_{r2} > t'_{r1}$, corresponding to α>1. The greater the relative retention, the greater the separation between the analyte components. Relative retention is generally independent of flow rate and can therefore be used to help identify peaks when the flow rate changes. For each peak in a chromatogram, the capacity factor k' is given as $$k' = \frac{t_r - t_m}{t_m};$$

which is to say that the capacity factor is the ratio of the time the solute spends in the stationary phase relative to the time the solute spends in the mobile phase. Accordingly, the longer a component is retained by the chromatographic field, the greater the capacity factor. This gives rise to the partition coefficient $$K = \frac{C_s}{C_m}$$

which corresponds to the ratio of solute concentration in the stationary phase $C_s$ relative to the concentration in the mobile phase $C_m$. Accordingly, the greater the ratio of partition coefficients between mobile and stationary phases, the greater the separation between two components of a mixture.

Given a chromatographic field of infinite permeability and cross-sectional area A that extends from x to x+l (where l represents the linear transport distance of the flow-path), the volume of the chromatographic field may be expressed as V=Al. Let the concentration at point x of analyte solute component G be [G] at time t. Accordingly, the number of particles that enter the chromatographic field per unit time is JA where J is the solute particle flux. Therefore, the rate of increase in molar concentration inside the chromatographic field due to the incoming particle flux is $$\left.\frac{\partial [G]}{\partial t}\right|_x = \frac{JA}{Al} = \frac{J}{l}.$$

Consider also an out-bound flux of solute particles at the x+l surface of the chromatographic field which may be similarly derived as $$\left.\frac{\partial [G]}{\partial t}\right|_{x+l} = \frac{J'A}{Al} = \frac{J'}{l}.$$

Therefore, the net time-rated change of concentration (e.g. the 'concentration velocity') may be expressed as:

$$\frac{\partial [G]}{\partial t} = \frac{J - J'}{l}$$

Suppose: (1) that the flux of solute particles J diffusing inside the chromatographic field comprises motion in response to a thermodynamic force $\mathscr{F}$ arising from a concentration gradient; (2) that the analyte particles reach a steady-state drift speed s when the thermodynamic force $\mathscr{F}$ is matched by the viscous drag; (3) that the drift speed s is proportional to the thermodynamic force $\mathscr{F}$; (4) that the solute particle flux J is proportional to the drift speed; and (5) that the thermodynamic force $\mathscr{F}$ is proportional to the spatial concentration gradient $$\frac{d[G]}{dx}.$$

The resulting chain of proportionalities $J \propto s$, $s \propto \mathcal{F}$, and $$\mathcal{F} \propto \frac{d[G]}{dx}$$

implies that the solute particle flux J is proportional to the concentration gradient $$\frac{d[G]}{dx},$$

which will be apparent to skilled artisans as corresponding to 'Fick's First Law of Diffusion'. The constant of proportionality is given as the diffusion coefficient $\mathcal{D}$ in the equation $$J = \mathcal{D}\frac{d[G]}{dx}$$

for diffusion restricted to a single dimension x. Therefore, the expression J−J' taken from the expression for the diffusive concentration velocity becomes $$\mathcal{D}\frac{d[G]'}{dx} - \mathcal{D}\frac{d[G]}{dx}.$$

Substitution of the linear accumulation of solute particle concentration over the length of the chromatographic field yields $$J - J' = \mathcal{D}\frac{d}{dx}\left([G] + \frac{d[G]}{dx}l\right) - \mathcal{D}\frac{d[G]}{dx}$$

which further reduces to $$J - J' = \mathcal{D}l\frac{d^2[G]}{dx^2}.$$

This expression may then be substituted back into the concentration velocity expression to give:

$$\frac{d[G]}{dt} = \frac{J - J'}{l} = \mathcal{D}\frac{d^2[G]}{dx^2} = \mathcal{D}\nabla_x^2[G]$$

which will be apparent to skilled artisans as the time dependent diffusion equation according to 'Fick's Second Law of Diffusion' and relates the concentration velocity at any point to the spatial variation of the concentration at that point. More generally, this may be appreciated as a physical basis for the typically observed behavior of diffusing chemical species translating away from areas of relative high concentration to areas of relative lower concentration (e.g., "moving down the concentration gradient").

Next, consider the time dependence of the partial molecular pressure p of an eluting component G from a chromatographic field of given volume V. The 'Ideal Gas Law' PV=nRT, which for molecular-scale systems rather than for large aggregates of particles (i.e., moles of molecules), becomes pV=nkT wherein: p is the partial molecular pressure; V is the volume of the container providing spatial boundary conditions; n is the number of particles; k is the Boltzmann constant; and T is the temperature. Solving for the partial pressure yields $$p = \frac{nkT}{V}.$$

After taking the partial derivative with respect to time at constant temperature and volume, the following expression for the pressure velocity may be obtained:

$$\left.\frac{\partial p}{\partial t}\right)_{T,V} = \frac{\partial\left(\frac{nkT}{V}\right)}{\partial t} = \frac{kT}{V}\frac{\partial n}{\partial t}$$

For an eluting analyte solute that is not replenished over time as the solute escapes, the time-rated change of the number of solute particles is given as $$\frac{\partial n}{\partial t} = -Z_w A_o,$$

where $Z_w$ is the collisional frequency associated with the mean free path of the solute particles and $A_o$ is the area of the opening that the solute particles have available for elution from the chromatographic field. The collisional frequency is related to the partial pressure of the solute particles p, the mass of the particles m and the temperature of the system T by the equation $$Z_w = \frac{p}{\sqrt{2\pi mkT}}.$$

Substitution of this relation back into the expression for the pressure velocity yields $$\frac{\partial p}{\partial t} = \frac{-pA_0}{V}\sqrt{\frac{kT}{2\pi m}}$$

which integrates over time to $$p = p_0 e^{\frac{-t}{\tau}}, \text{ where } \tau = \frac{V}{A_0}\sqrt{\frac{2\pi m}{kt}}.$$

From this expression for the pressure velocity, the following may generally be observed: (1) if the eluent (e.g., solvent and sample) is not replenished, the pressure decreases exponentially to zero; (2) the pressure velocity is faster with increasing temperature and slower with decreasing temperature; (3) the pressure velocity is slower with heavier solute particles and faster with less massive particles; (4) the pressure velocity is faster with increasing surface area of the chromatographic field and slower with decreased surface area; and (5) the pressure velocity is slower with increasing volume of the chromatographic field and faster with decreasing volume.

At constant temperature, the time derivative of the expression for the partial pressure $$p = \frac{nkT}{V} \text{ becomes:}$$

$$\left.\frac{\partial p}{\partial t}\right)_T = kT\frac{\partial\left(\frac{n}{V}\right)}{\partial t} = kT\frac{\partial[G]}{\partial t}$$

Therefore, substituting the expression corresponding to Fick's Second Law of Diffusion for the concentration velocity previously derived, the generalized expression for the pressure velocity of solute particles diffusing in three dimensions in a chromatographic field of infinite permeability as a function of concentration of the solute particles [G] may be represented as:

$$\left.\frac{dp}{dt}\right)_T = -kT\mathcal{D}_G\nabla^2[G] = -kT\mathcal{D}_G\left(\frac{\partial^2}{\partial x^2}+\frac{\partial^2}{\partial y^2}+\frac{\partial^2}{\partial z^2}\right)[G]$$

If, however, the chromatographic field is assumed to have finite diffusive permeability (indeed, as generally required for achieving chromatographic separation), an additional diffusion coefficient $\hat{D}_{\Xi(a,b,c\ldots)}$ may be included to account for various permeability metrics such as, for example: the number of chromatographic theoretical plates, chromatographic plate height, stationary phase adsorption, non-uniform porosity; anisotropic transport along different dimensions; hydrophobicity; capillary defects; etc.

For example, consider the expression for a biomolecular component $\mathcal{B}$ diffusing through a chromatographic field (or otherwise porous barrier) Ξ:

$$\left.\frac{dp}{dt}\right)_{\Xi,\mathcal{B}}^{diffusion} = -kT\left(\hat{D}_{\Xi(a,b,c\ldots)}\mathcal{D}_{\mathcal{B}}\right)\left(\frac{\partial^2}{\partial x^2}+\frac{\partial^2}{\partial y^2}+\frac{\partial^2}{\partial z^2}\right)[\mathcal{B}]$$

Upon inspection, this expression relates the concentration of the biomolecular component $\mathcal{B}$ at any point within the chromatographic field (or otherwise porous barrier) Ξ to the three dimensional variation of biomolecular component $\mathcal{B}$ concentration at that point; which is to say that $\mathcal{B}$ will passively diffuse through a chromatographic field so as to move down its concentration gradient from volume elements comprising higher $\mathcal{B}$ concentration to volume elements comprising relative lower $\mathcal{B}$ concentration.

Substitution of $A_\Xi l$ for the volume V in the effusion equation $$\frac{dp}{dt} = \frac{-pA_0}{V}\sqrt{\frac{kT}{2\pi m}} \text{ yields } \frac{dp}{dt} = \frac{-pA_0}{A_\Xi \ell}\sqrt{\frac{kT}{2\pi m}}.$$

If the ratio of the area of the aggregate void-volume to the aggregate surface area of the chromatographic field is taken to be a dimensionless quantity θ corresponding to the porosity of the chromatographic field, a composite expression for elution of biomolecular component $\mathcal{B}$ becomes:

$$\left.\frac{dp}{dt}\right)_{\Xi,\mathcal{B}}^{elution} = -p_{\mathcal{B}}\theta_\Xi\sqrt{\frac{kT}{2\pi m_{\mathcal{B}}\ell_\Xi^2}}$$

and relates the pressure of $\mathcal{B}$ that elutes through the chromatographic field (or otherwise porous barrier) Ξ to: the back-side pressure of the biomolecular component $p_{\mathcal{B}}$; the temperature T; the mass of the biomolecular component $m_{\mathcal{B}}$; the linear transport distance of the chromatographic field l; and the porosity of the chromatographic field $\theta_\Xi$. Accordingly, the biomolecular analyte solute $\mathcal{B}$ will generally: (1) elute more rapidly at higher operating temperatures and more slowly at lower temperatures; (2) elute more rapidly with increased back-side pressure of $\mathcal{B}$ and more slowly with decreased back-side pressure; (3) elute more rapidly with chromatographic fields having increased porosity and more slowly with decreased porosity; and (4) elute more rapidly with porous chromatographic fields having decreased linear transport distances (e.g., shorter columns) and more slowly with increased transport distances.

Plate height $$H = \frac{\sigma^2}{x},$$

where σ is the standard deviation and x is the linear transport distance along the flow-path, is a measure of how well chromatographic bands of analyte solute may be separated on a particular chromatographic field. The number of plates for a Gaussian peak is generally given as $$N = 16\frac{t_r^2}{w^2},$$

where $t_r$ is the retention time and w is the peak width (typically taken as four standard deviations at the baseline; e.g., 4σ). Resolution of neighboring peaks becomes the difference in retention time divided by the average width w measured at the baseline. Resolution is proportional to $\sqrt{N}$ and also generally increases with relative retention and capacity factor. Accordingly, doubling the length of a chromatographic field generally increases resolution by a factor of approximately $\sqrt{2}$.

The standard deviation of a diffusing band of solute generally corresponds to $\sigma=\sqrt{2Dt}$, where D is the composite diffusion coefficient and t is time. The van Deemter equation describes band broadening on a chromatographic field as:

$$H \approx A + \frac{B}{u_x} + Cu_x$$

where H is the plate height, $u_x$ is the linear flow rate along the linear transport path of the chromatographic field, and A, B and C are constants: A representing irregular flow paths, B representing longitudinal diffusion and C representing the finite rate of transfer of analyte solute between mobile and stationary phases for a given column. The optimum flow rate, which generally minimizes plate height, is faster for gas chromatography than for liquid chromatography. The number of plates and the optimal flow rate usually increases as the stationary-phase particle size is decreased. Open tubular columns typically provide higher resolution and shorter analysis times than packed columns. In general, bands spread not only on the chromatographic field but also during sample injection as well as during component analyte detection. Overloading and tailing may be corrected by inter alia using smaller sarhples or by masking strong adsorption sites on the stationary phase. Additionally, there are several underlying processes that may impact the plate height, such as, for example: longitudinal diffusion; resistance to mass transfer in the mobile and/or stationary phase; and eddy diffusion.

To monitor the performance of a particular column, it is usually a recommended practice to periodically measure the capacity factor of a standard sample, the number of theoretical plates and/or peak asymmetry. Variations in any of these values generally indicate degradation of the chromatographic field over time and/or repeated use.

The majority of conventional detection systems in separation science are generally employed for single-point detection at or near the end of a chromatographic field; such as the analytical output of gas chromatography or capillary electrophoresis. However, at least one FF multiple-discrete-point detection method along the linear transport path of, for example, a electrophoretic separation system is known to have generally demonstrated improved S/N utilizing multiplex detection, signal averaging and Fourier analysis. See, for example, H. J. Crabtree, M. U. Kopp, and A. Manz; *Anal. Chem.*, 71, 2130, 1999. As used herein, the term "chromatographic field" may be understood to include any system and/or method for electrophoretic separation as well.

Transform Analysis

In mathematics and physics, pairs of functions are often encountered which may be related by an expression of the form $$g(\alpha) = \int_a^b f(t) K(\alpha, t) dt$$

wherein the function $g(\alpha)$ is termed the "integral transform" of $f(t)$ by the kernel operator $K(\alpha,t)$. The operation may also be described as "mapping" a function $f(t)$ in t-space into another function $g(\alpha)$ in $\alpha$-space. It is generally believe that there are an infinite number of such transform operators; one of the most useful and best known of which is the Fourier transform:

$$g(\alpha) = \frac{1}{\sqrt{2\pi}} \int_{-\infty}^{\infty} f(t) e^{i\alpha t} dt$$

Two exemplary variants of the exponential kernel form are the Fourier cosine and Fourier sine transforms:

$$g_{cos}(\alpha) = \sqrt{\frac{2}{\pi}} \int_0^{\infty} f(t) \cos(\alpha t) dt$$

$$g_{sin}(\alpha) = \sqrt{\frac{2}{\pi}} \int_0^{\infty} f(t) \sin(\alpha t) dt$$

Transformation is generally based on the real and imaginary parts of the kernel $e^{i\alpha t}$ taken separately: $\cos(\alpha t)$ and $\sin(\alpha t)$. Because these kernels correspond to functions used to describe waves, Fourier transforms frequently appear in the study of wave mechanics and the analysis of information embedded in wave data; particularly when phase information is desired. For example, the electron distribution in an atom may be obtained from a Fourier transformation of the amplitude of scattered X-ray data.

Three other kernels that find frequent use are $e^{-\alpha t}$, $tJ_n(\alpha t)$ and $t^{\alpha-1}$, which respectively give rise to the Laplace transform $$g(\alpha) = \int_0^{\infty} f(t) e^{-\alpha t} dt,$$

the Hankel (e.g., Fourier-Bessel) transform $$g(\alpha) = \int_0^{\infty} f(t) t J_n(\alpha t) dt$$

and the Mellin transform $$g(\alpha) = \int_0^{\infty} f(t) t^{\alpha-1} dt.$$

Indeed, as previously stated, it is believed that an infinite number of such transforms exist.

Integral transforms are generally linear, e.g.:

$$\int_a^b [c_1 f_1(t) + c_2 f_2(t)] K(\alpha, t) dt =$$

$$\int_a^b c_1 f_1(t) K(\alpha, t) dt + \int_a^b c_2 f_2(t) K(\alpha, t) dt \int_a^b cf(t) K(\alpha, t) dt =$$

$$c \int_a^b f(t) K(\alpha, t) dt$$

where $c_1$ and $c_2$ are constants and $f_1(t)$ and $f_2(t)$ are functions for which the transform operation is defined. Substituting the operator $\mathcal{L}$ for the linear integral transform, the following expression may be obtained: $g(\alpha) = \mathcal{L} f(t)$. Accordingly, an inverse operation $\mathcal{L}^{-1}$ (e.g., a "deconvolution operator") is hypothesized to exist in an infinitely-dimensional Hilbert space such that $f(t) = \mathcal{L}^{-1} g(\alpha)$.

In the representative case of a Fourier transform, for a piecewise continuous function $F(x)$ over a finite interval $0 \leq x \leq \pi$, the finite Fourier cosine transform of $F(x)$ is given as:

$$f_{cos}(n) = \int_0^{\pi} F(x) \cos(nx) dx$$

(n=0, 1, 2, . . . )

If x ranges over the interval $0 \leq x \leq L$, substitution of $$x' = \frac{\pi x}{L}$$

generally allows the use of this definition as well. The inverse transform may accordingly be written as:

$$\overline{F}(x) = \frac{1}{\pi} f_{cos}(0) + \frac{2}{\pi} \sum_{n=1}^{\infty} f_{cos}(n) \cos(nx)$$

($0 < x < \pi$)
where $$\overline{F}(x) = \frac{[F(x+0) + F(x-0)]}{2}.$$

Therefore, $\overline{F}(x) = F(x)$ at points of continuity. The generalized formula becomes:

$$f_{cos}^{(2)}(n) = \int_0^{\pi} F''(x) \cos(nx) dx$$

$$= -n^2 f_{cos}(n) - F'(0) + (-1)^n F'(\pi)$$

and makes the finite Fourier cosine transform useful in certain boundary-value problems.

Similarly, the finite Fourier sine transform of F(x) on the same interval is given as:

$$f_{\sin}(n) = \int_0^\pi F(x)\sin(nx)dx$$

(n=1, 2, 3, ... ) with the inverse transform $$\overline{F}(x) = \frac{2}{\pi}\sum_{n=1}^\infty f_{\sin}(n)\sin(nx)$$

(0<x<π) correspondingly yielding $$f_{\sin}^{(2)}(n) = \int_0^\pi F''(x)\sin(nx)dx$$
$$= -n^2 f_{\sin}(n) - nF(0) - n(-1)^n F(\pi)$$

If F(x) is defined for $x \geq 0$ and is piecewise continuous over any finite interval, and if $$\int_0^\infty F(x)dx$$

is convergent, then $$f_{\cos}(\alpha) = \sqrt{\frac{2}{\pi}}\int_0^\infty F(x)\cos(\alpha x)dx$$

is said to be the Fourier cosine transform of F(x), wherein:

$$\overline{F}(x) = \sqrt{\frac{2}{\pi}}\int_0^\infty f_{\cos}(\alpha)\cos(\alpha x)d\alpha$$

An important property of the Fourier cosine transform is $$f_{\cos}^{(2r)}(\alpha) = \sqrt{\frac{2}{\pi}}\int_0^\infty \left(\frac{d^{2r}F}{dx^{2r}}\right)\cos(\alpha x)dx$$
$$= -\sqrt{\frac{2}{\pi}}\sum_{n=1}^{r-1}(-1)^n a_{2r-2n-1}\alpha^{2n} + (-1)^r \alpha^{2r} f_{\cos}(\alpha)$$

where the limit of $$\lim_{x\to 0}\frac{d^r F}{dx^r} = a_r$$

makes this expression useful in practical applications.

Accordingly, $$f_{\sin}(\alpha) = \sqrt{\frac{2}{\pi}}\int_0^\infty F(x)\sin(\alpha x)dx$$

defines the Fourier sine transform of F(x), with $$\overline{F}(x) = \sqrt{\frac{2}{\pi}}\int_0^\infty f_{\sin}(\alpha)\sin(\alpha x)d\alpha,$$

and in similar fashion:

$$f_{\sin}^{(2r)}(\alpha) = \sqrt{\frac{2}{\pi}}\int_0^\infty \left(\frac{d^{2r}F}{dx^{2r}}\right)\sin(\alpha x)dx$$
$$= -\sqrt{\frac{2}{\pi}}\sum_{n=1}^r (-1)^n a_{2r-2n}\alpha^{2n-1} + (-1)^{r-1}\alpha^{2r} f_{\sin}(\alpha)$$

If F(x) is defined for $-\infty < x < \infty$, and if $$\int_{-\infty}^\infty F(x)dx$$

is absolutely convergent, then $$f(\alpha) = \frac{1}{\sqrt{2\pi}}\int_{-\infty}^\infty F(x)e^{i\alpha x}dx$$

is said to be the Fourier transform of F(x) with the inverse function $$\overline{F}(x) = \frac{1}{\sqrt{2\pi}}\int_{-\infty}^\infty f(\alpha)e^{-i\alpha x}d\alpha.$$

Where x represents data in time-space and α represents data in frequency-space, $\overline{F}(x)$ may be used to produce, for example, frequency-domain output from time-domain input.

Chemical and Instrumental Noise

In general, two types of noise corresponding to chemical analyses may exist: chemical noise and instrumental noise. Chemical noise arises from a variety of generally uncontrollable variables that affect the chemistry of the analyte system. Examples include inter alia undetected variations in temperature or pressure that affect the position of chemical equilibria, fluctuations in humidity that cause changes in the moisture content of samples, vibrations that lead to stratification of powdered solids, and changes in light intensity that affect photosensitive materials. Instrumental noise, on the other hand, arises from the design and/or use of the analytical instrument itself.

Noise is usually associated with each component of an analytical instrument, for example: the source, input transducers; signal-processing elements; output transducers, etc. Certain types of instrumental noise include, for example: thermal noise (e.g., Johnson noise); shot noise; flicker noise; and environmental noise.

Thermal noise is generally caused by thermal disturbance of electrons or other charge carriers in resistors, capacitors, radiation detectors, electrochemical cells and/or other resistive elements in an instrument. This agitation of charged particles is usually random and periodically creates charge inhomogeneities, which in turn create voltage fluctuations that may appear in the detector trace as noise. It is important to note that thermal noise is present even in the absence of any current in a resistive element at any temperature above absolute zero.

The magnitude of thermal noise is readily obtained from thermodynamic considerations and is generally given as $v_{rms} = \sqrt{4kTR\Delta f}$, where $v_{rms}$ is the root-mean-square noise voltage residing in a frequency bandwidth $\Delta f$, k is the Boltzmann constant, T is the temperature, and R is the resistance of the circuit element. To carry information, an instrument typically must have a finite bandwidth of $\Delta f$.

This bandwidth is inversely related to the rise time $t_r$ of the instrument as given by $$\Delta f = \frac{1}{t_r}.$$

The rise time $t_r$ corresponding to the instrument's response time to abrupt changes in input. Normally, the rise time is taken as the time required for the output to increase from about %10 to about 90% of the final value. Thus, if the rise time is 0.01 seconds, the bandwidth is about 100 Hz. Accordingly, thermal noise may be decreased by narrowing the bandwidth; however, as the bandwidth narrows, the instrument becomes slower to respond to a signal change thereby generally requiring more time to obtain a reliable signal measurement.

Thermal noise may also be reduced by lowering the electrical resistance of circuit elements and/or by lowering their temperature. For example, lowering the temperature of a detector from room temperature (298K) to the temperature of liquid nitrogen (77K) will reduce the noise by about 50%. It is important to note that thermal noise, although generally dependent upon the frequency bandwidth, is typically independent of frequency itself. Accordingly, thermal noise is sometimes termed "white noise" by analogy to white light, which contains all visible frequencies.

Shot noise may be encountered when a current involves the movement of electrons or other charged particles across a junction. In a typical electronic circuit, these junctions are found at p and n interfaces; in photocells and vacuum tubes, the junction consists of the evacuated space between the anode and cathode. The currents in such devices typically concern a series of quantized events—namely, the transfer of discrete electrons across the junction. These events, however, are generally random and the rate at which they occur is accordingly subject to statistical fluctuations, which may be described by the expression $i_{rms} = \sqrt{2Ie\Delta f}$, where $i_{rms}$ is the root-mean-square current fluctuation associated with the average direct current I, e is the charge of the electron, and $\Delta f$ again is the bandwidth of frequencies being considered. Accordingly, shot noise in a current measurement may generally only be minimized by reducing the bandwidth. Like thermal noise, shot noise is also said to have a "white" spectrum.

Flicker noise is characterized as having a magnitude that is inversely proportional to the frequency of the signal being observed and is sometimes termed $$"\frac{1}{f}\text{ noise"}$$

as a consequence. The causes of flicker noise are generally not well understood, however, the ubiquitous presence of flicker noise is typically recognizable by its frequency dependence. Flicker noise becomes significant at frequencies lower than about 100 Hz. The long-term drift observed in, for example: DC amplifiers; meters; and galvanometers is generally believed to be a manifestation of flicker noise. Flicker noise may be reduced significantly by using inter alia wire-wound or metallic film resistors rather than the conventional composition type.

Environmental noise is generally a composite of noises arising from the surroundings. Much of this type of noise occurs because each conductor in an instrument is potentially an antenna capable of picking up radiation and converting it to a signal in the detection domain. Numerous sources of radiant energy exist in the environment, including, for example: AC power lines; radio and television stations; combustion engine ignition systems; arcing switches; brushes in electrical motors; lightning; and ionospheric disturbances to name just a few. Note, however, that some of these sources, such as power lines and radio stations, cause noise even with limited-frequency bandwidths.

Multiplex Detection

Multiplex analytical instruments are generally single-channel devices in which signal elements are usually observed simultaneously. The term "multiplex" comes from data communications theory where it has been used to describe systems in which multiple information sets are transported substantially simultaneously. For an analytical instrument, in order to determine the value of individual signal elements, an analyte signal may be modulated in a fashion that permits subsequent decoding of the signal to yield information embedded therein. It is important to note, however, that use to the term "multiplexing" is not intended to be restricted to description of systems in which all signal elements are observed simultaneously; for example, the term "multiplexing" may also be used to indicate any system or method in which any number of independent signals may be encoded and/or transmitted over a substantially single data traffic medium.

Most multiplex instruments depend on, for example, Fourier transformations for signal decoding and are consequently often termed "Fourier transform instruments". Indeed, Fourier transform devices have been developed for a wide variety of analytical methods, including nuclear magnetic resonance and mass spectroscopy as well as for certain types of electro-analytical measurements. In optical spectroscopy, de-convolution of modulated data has also been performed with the so-called Hadamard and/or Hilbert transforms as well; however, these techniques have generally found less widespread application to date.

Fourier transform spectroscopy was first developed by astronomers in the early 1950's in order to study the infrared spectra of distant stars. The first chemical applications of Fourier transform spectroscopy, reported approximately a decade later, were in the energy-starved far-infrared region. By the late 1960's, Fourier instruments for chemical studies in both the far-infrared ($10\text{ cm}^{-1}$–$400\text{ cm}^{-1}$) and the ordinary infrared regions became commercially available. For a more detailed discussion of Fourier transform spectroscopy, see, for example, A. G. Marshall and F. R. Verdon, *Fourier Transform in NMR, Optical, and Mass Spectrometty*, 1990; P. R. Griffiths, *Chemical Fourier Transform Spectroscopy*, 1975; P. R. Griffiths, *Transform Techniques in Chemistty*, 1978; A. G. Marshall, *Fourier, Hadamard and Hilbert Transforms in Chemistry*, 1982. Descriptions of Fourier transform instruments for the ultraviolet and visible spectral regions may also be found, for example, in A. P. Thorne, *Anal. Chem.*, 63, 57A, 1991; however, ultraviolet Fourier spectroscopy adoption has generally been less popular than other conventional transform spectroscopic techniques.

In general, three major advantages correspond to the use of multiplex detection techniques. The first is the Jaquinot advantage, which is realized because transform instruments have fewer optical elements than their dispersive counterparts (e.g., the power of radiation reaching the detector is generally much greater). A second advantage of transform instruments is improved wavelength accuracy and precision arising from inter alia signal averaging, thereby improving S/N. The third advantage, often called the Fellgett advantage, is achieved as a result of substantially simultaneous data signal detection, thereby making it possible to acquire an entire spectrum in a brief period (often 1 second or less).

Consider an experimentally derived spectrum as being made up of m individual transmittance measurements at equally spaced frequency or wavelength intervals called "resolution elements". The quality of the spectrum (e.g., the amount of spectral detail) increases as the number of resolution elements becomes larger and, alternatively or conjunctively, as the frequency intervals between measurements become smaller. Thus, in order to realize enhanced spectral resolution, m may be made larger. However, increasing the number of resolution elements correspondingly increases the time required for acquiring a spectrum with, for example, a scanning instrument.

Consider also, for example, the acquisition of an infrared spectrum in the range of 500 cm$^{-1}$ to 5000 cm$^{-1}$. If resolution elements of 3 cm$^{-1}$ are chosen, m would be about 1500; however, if 0.5 seconds were required for recording the transmittance of each resolution element, about 12.5 minutes would be needed to acquire the spectrum. Reducing the width of the resolution element in half to about 1.5 cm$^{-1}$ would be expected to provide substantially greater spectral detail, and would generally double the number of resolution elements as well as the time required for their measurement.

For most FF optical instruments, decreasing the width of the resolving element generally has the unfortunate effect of also decreasing the S/N ratio inasmuch as narrower apertures, which lead to weaker signals reaching the transducer, generally must be used. For infrared detectors, the reduction in signal strength is generally not accompanied by a corresponding decrease in noise; accordingly, a degradation in S/N results.

The S/N ratio for an average of n measurements is given by $$\frac{S}{N} = \sqrt{n}\,\frac{S_x}{N_x},$$

where $S_x$ and $N_x$ are the averaged signal and the averaged noise, respectfully. Unfortunately, the application of signal averaging to dispersive spectroscopy is typically costly in terms of acquisition time. Thus, in the example previously considered wherein 12.5 minutes were required to obtain a spectrum of 1500 resolution elements—to improve the S/N ratio by a factor of 2 would generally require averaging at least 4 spectra, which accordingly would then generally require about 50 minutes of signal acquisition time.

Transform spectroscopy differs from conventional dispersive spectroscopy in that the resolution elements for a spectrum are generally measured simultaneously, thereby dramatically reducing the time required to derive a spectrum for any given S/N ratio. An entire spectrum of about 1500 resolution elements may be recorded in about the time typically required to observe a single element with dispersive instruments. The corresponding savings in acquisition time is often employed to enhance the S/N of the analyte signal; for example, in the 12.5 minutes required to derive a spectrum in the earlier example, 1500 transform spectra generally may be recorded and averaged. The improvement in S/N would in principle be on the order of about $\sqrt{1500}$ (e.g., a factor of approximately 39). This representative advantage of transform spectroscopy was first recognized by P. Feligett in 1958. It is worth noting here that the theoretical $\sqrt{n}$ improvement of S/N is seldom realized in practical application; however, significant improvements in S/N have generally been observed with transform spectroscopic techniques.

Conventional dispersive spectroscopy may be termed "frequency domain" spectroscopy in that radiant power signals are recorded as a function of frequency (or, alternatively, as the inversely related wavelength). In contrast, "time domain" spectroscopy is concerned with changes in detector signal as a function of time.

Molecular Energy Partition Function

The total energy E associated with a molecule is the sum of the individual energy components $E_i$ summed over n modes of the molecular system:

$$E = \sum_{i=1}^{n} E_i = E_{electronic} + E_{vibrational} + E_{rotational} + E_{translational}$$

where $E_{electronic}$ describes the electronic energy of the molecule arising from electronic states populated by the electrons, $E_{vibrational}$ refers to the energy associated with the inter-atomic vibrational states, $E_{rotational}$ refers to the energy contribution of rotational motions of the molecule, and $E_{translational}$ corresponds to the net momentum of the molecule. This separation is generally approximate (except for translation) because the modes are usually not completely independent. The separation of the electronic and vibrational motions, for example, is justified by the well-known Born-Oppenheimer approximation, while the separation of the vibrational and rotational modes is generally valid where the molecule may be considered to be a rigid rotor.

Absorption and Emission of Radiation

As resonantly tuned energy is introduced to a molecular system, various energy absorption mechanisms may occur to induce intramolecular state-to-state transitions within the available energy manifolds: for example, electronic transitions; vibrational transitions; rotational transitions; etc. In other intramolecular processes, absorbed energy may subsequently be released from the molecule to the external environment in order to stabilize or otherwise lower the total energy of the system. Accordingly, various analytical techniques have been adapted to monitor or otherwise detect endergonic intra-molecular transitions (e.g., absorption spectroscopies) as well as exergonic transitions (e.g., emission spectroscopies).

Consider a representative collection of N two-level systems in a volume of one cubic meter with upper energy $E_1$ and lower energy $E_0$—both at constant temperature T and exposed to a radiation density $\rho_\upsilon(T)$. Given the system is assumed to be in thermal equilibrium, if the number of sub-systems with energy $E_1$ is $N_1$ and the number of sub-systems with energy $E_0$ is $N_0$, then the populations $N_1$ and $N_0$ $$\left(\text{for } N = \sum_{n=0}^{1} N_n\right)$$

are generally related by the expression $$\frac{N_1}{N_0} = e^{-\frac{h\upsilon_{10}}{kT}},$$

wherein $h\upsilon_{10} = E_1 - E_0$. Skilled artisans will appreciate this expression as corresponding to the well-known Boltzmann distribution for thermal equilibrium.

Accordingly, there are three possible processes that may change the state of the system from $E_0$ (e.g., the "ground state") to $E_1$ (e.g., the "excited state"); or, alternatively, from $E_1$ to $E_0$: absorption, spontaneous emission and stimulated emission. Absorption results from the presence of a radiation density $\rho_\upsilon(\upsilon_{10})$ of a frequency corresponding to the transition from the ground state to the excited state at the rate $$\frac{d}{dt}N_1 = B_{0\to 1}\rho_\upsilon(\upsilon_{10})N_0.$$

The coefficient $B_{0\to 1}$ is thus termed a "rate constant", and is commonly referred to as the Einstein absorption coefficient or "Einstein B coefficient". Similarly, if the system is already in an excited state, then a photon of energy $h\upsilon_{10}$ (incident from the external radiation density $\rho_\upsilon$) may induce the system to undergo the transition from the excited state to the ground state. The rate for stimulated emission is generally given by $$\frac{d}{dt}N_1 = -B_{0\to 1}\rho_\upsilon(\upsilon_{10})N_1,$$

in which $B_{1\to 0}$ is the stimulated emission coefficient. Finally the system in the excited state may spontaneously emit a photon at a rate generally corresponding to $$\frac{d}{dt}N_1 = -A_{1\to 0}N_1.$$

Since the system is at equilibrium, the population flux of the excited state by absorption must balance the rate of depopulation by stimulated and/or spontaneous emission, so that $N_0 B_{0\to 1}\rho_\upsilon = A_{1\to 0}N_1 + B_{1\to 0}\rho_\upsilon N_1$ and hence:

$$\frac{N_1}{N_0} = \frac{B_{0\to 1}\rho_\upsilon}{A_{1\to 0}+B_{1\to 0}\rho_\upsilon} = e^{-\frac{h\upsilon_{10}}{kt}}$$

Solving for $\rho_\upsilon$ yields $$\rho_\upsilon(\upsilon_{10}) = \frac{A_{1\to 0}}{B_{0\to 1}e^{\frac{h\upsilon_{10}}{kt}} - B_{1\to 0}};$$

however, $\rho_\upsilon(\upsilon_{10})$ also finds expression in the Planck relation corresponding to $$\rho_\upsilon(\upsilon_{10}) = \frac{8\pi h\upsilon_{10}^3}{c^3\left(e^{\frac{h\upsilon_{10}}{kt}} - 1\right)}.$$

In order for both expressions for the radiation density $\rho_\upsilon(\upsilon_{10})$ to be valid, $B_{0\to 1}=B_{1\to 0}$ and $$A_{1\to 0} = \frac{8\pi h\upsilon_{10}^3}{c^3}B_{0\to 1}.$$

Accordingly, the rate constants for absorption and stimulated emission—two ostensibly different physical processes—are identical. Moreover, the spontaneous emission rate (e.g., the "excited state lifetime") may be determined from the absorption coefficient. Note, however, that the factor $\upsilon_{10}^3$ plays an important role in the competition between induced and spontaneous emission processes.

The interaction of electromagnetic radiation with matter may be described by a semi-classical model wherein the energy levels of molecules may be obtained by solution of the well-known, time-independent Shrödinger equation $\hat{H}\psi_n = E_n\psi_n$ for the $n^{th}$ energy state, while, for example, electromagnetic radiation is treated classically. A two-level system may generally be described by lower and upper state wavefunctions $\psi_0$ and $\psi_1$, corresponding to the ground state and the excited state respectively. Electromagnetic radiation complying with the Bohr condition $E_1 - E_0 = h\upsilon = \hbar\omega$ may be applied to the system to induce a transition from the lower energy state $E_0$ to the upper energy state $E_1$.

The molecule of interest generally comprises nuclei and electrons at positions $r_i$ possessing charges $q_i$. The system as a whole thus has a net dipole moment $\mu$ with Cartesian components corresponding to:

$\mu_x = \Sigma x_i q_i$ $\mu_y = \Sigma y_i q_i$ $\mu_z = \Sigma z_i q_i$ where x, y and z are the coordinates of the particles relative to the center of mass for the molecule. The interaction of the radiation with the molecular system is taken into account by the addition of a time-dependent perturbation to the Hamiltonian operator $\hat{H}$ according to:

$$\hat{H}' = -\mu \cdot E(t)$$
$$= -\mu \cdot E_0\cos(k\cdot r - \omega t)$$

If the oscillating electric field is in the z direction and center of mass of the molecular system is disposed at the origin r=0 (assuming $\lambda \gg$ dimensions of the system in order to avoid accounting for differing field strengths at different parts of the molecule), then the time-dependent perturbation becomes:

$$\hat{H}' = -\mu_z E_{0z}\cos(\omega t)$$
$$= -\mu E\cos(\omega t)$$

The transition probability between the two states may be obtained by solving the time-dependent Shrödinger equation $$i\hbar\frac{\partial\Psi}{\partial t} = [\hat{H} + \hat{H}'(t)]\Psi.$$

In the absence of the perturbation $\hat{H}'$, the two time-dependent solutions are:

$$\Psi_0 = \psi_0 e^{\frac{-iE_0 t}{\hbar}} = \psi_0 e^{-i\omega_0 t}$$
$$\Psi_0 = \psi_1 e^{\frac{-iE_1 t}{\hbar}} = \psi_1 e^{-i\omega_1 t}$$

with $\omega_i = \frac{E_i}{\hbar}$.

The wavefunction for the perturbed system may be given by the linear combination of the complete set of functions $\Psi_0$ and $\Psi_1$:

$$\Psi(t) = a_0(t)\psi_0 e^{\frac{-iE_0 t}{\hbar}} + a_1(t)\psi_1 e^{\frac{-iE_1 t}{\hbar}} = a_0\psi_0 e^{-i\omega_0 t} + a_1\psi_1 e^{-i\omega_1 t}$$

where $a_0$ and $a_1$ are time-dependent coefficients. Substitution of the immediately preceding solution into the time-dependent Shrödinger equation yields:

$$i\hbar(\dot{a}_0\psi_0 e^{-i\omega_0 t} + \dot{a}_1\psi_1 e^{-i\omega_1 t}) = \hat{H}'a_0\psi_0 e^{-i\omega_0 t} + \hat{H}'a_1\psi_1 e^{-i\omega_1 t}$$

Multiplication by $\psi^*_0 e^{i\omega_0 t}$ or $\psi^*_1 e^{i\omega_1 t}$ followed by integration over all space yields a pair of coupled differential equations:

$$i\hbar \dot{a}_0 = a_0 \langle \psi_0 | \hat{H}' | \psi_0 \rangle + a_1 \langle \psi_0 | \hat{H}' | \psi_1 \rangle e^{-i\omega_{10} t}$$

$$i\hbar \dot{a}_1 = a_0 \langle \psi_1 | \hat{H}' | \psi_0 \rangle e^{i\omega_{10} t} + a_1 \langle \psi_1 | \hat{H}' | \psi_1 \rangle$$

If the time-dependent perturbation $\hat{H}'$ is taken as $-\mu E \cos(\omega t)$ in the electric-dipole approximation, then $\hat{H}'$ is observed to have odd parity. In other words, $\hat{H}'$ is an odd function since $\mu = ez$, while the products $|\psi_1|^2$ or $|\psi_0|^2$ are even functions; therefore, the integrands $\psi^*_1 \hat{H}' \psi_1$ and $\psi^*_0 \hat{H}' \psi_0$ are odd functions. All atomic and molecular states are understood to have definite parity (either even or odd) with respect to inversion in the space-fixed coordinate system such that:

$$\langle \psi_0 | \hat{H}' | \psi_0 \rangle = \langle \psi_1 | \hat{H}' | \psi_1 \rangle = 0$$

Accordingly, the immediately preceding coupled equations may be reduced to:

$$i\hbar \dot{a}_0 = -a_1 M_{01} E e^{-i\omega_{10} t} \cos(\omega t)$$

$$i\hbar \dot{a}_1 = -a_0 M_{01} E e^{i\omega_{10} t} \cos(\omega t)$$

The integral $M_{01} = M_{10} = \langle \psi_1 | \mu | \psi_0 \rangle$ is given as the dipole moment transition probability and is generally regarded as an important factor in determining selection rules and line intensities. Typically, $M_{10}$ is a vector quantity and the symbol $\mu_{10}$ ($\equiv M_{10}$) is often used. It is convenient to define $$\omega_R = \frac{M_{10} E}{\hbar}$$

as the Rabi frequency, which in combination with the identity relation $$\cos(\omega t) = \frac{e^{i\omega t} + e^{-i\omega t}}{2} \text{ yields:}$$

$$\dot{a}_0 = \frac{i a_1 \omega_R (e^{-i(\omega_{10} - \omega)t} + e^{-i(\omega_{10} + \omega)t})}{2}$$

$$\dot{a}_1 = \frac{i a_0 \omega_R (e^{i(\omega_{10} - \omega)t} + e^{i(\omega_{10} + \omega)t})}{2}$$

An approximation may be made by noting that $\omega_{10} \approx \omega$, since the system with Bohr frequency $$\frac{(E_1 - E_0)}{\hbar} = \omega_{10}$$

is resonant or nearly resonant with the optical angular frequency $\omega = 2\pi\upsilon$. The terms $e^{i(\omega_{10} - \omega)t}$ and $e^{-i(\omega_{10} - \omega)t}$ thus correspond to slowly varying functions of time compared to the rapidly oscillating non-resonant terms $e^{i(\omega_{10} + \omega)t}$ and $e^{-i(\omega_{10} + \omega)t}$. In what is commonly known as the rotating wave approximation, the non-resonant high-frequency terms may be neglected inasmuch as their effects essentially average to zero since they are rapidly oscillating functions of time. Defining $\Delta = \omega - \omega_{10}$ the immediately preceding time derivatives take the form:

$$\dot{a}_0 = \frac{i \omega_R e^{i\Delta t}}{2} a_1$$

$$\dot{a}_1 = \frac{i \omega_R e^{-i\Delta t}}{2} a_0$$

Skilled artisans will appreciate that these equations may be solved analytically. The difference $\Delta = \omega - \omega_{10}$ is often referred to as the "de-tuning frequency" since it measures how far, for example, electromagnetic radiation of frequency $\omega$ is tuned away from the resonance frequency $\omega_{10}$. The solution to these simultaneous first-order differential equations, with initial conditions $a_0(0) = 1$ and $a_1(0) = 0$ for the system initially in the ground state at $t=0$, is given as:

$$a_0(t) = e^{\frac{i\Delta t}{2}} \left[ \cos\left(\frac{\Omega t}{2}\right) - i\left(\frac{\Delta}{\Omega}\right) \sin\left(\frac{\Omega t}{2}\right) \right] \text{ and } a_1(t) = i\left(\frac{\omega_R}{\Omega}\right) \sin\left(\frac{\Omega t}{2}\right) e^{\frac{-i\Delta t}{2}}$$

where $\Omega = \sqrt{\omega_R^2 + \Delta^2}$. Skilled artisans will further appreciate that these solutions may be readily verified by straightforward substitution.

The time-dependent probability that the system will be found in the excited state may be expressed as $$|a_1(t)|^2 = \frac{\omega_R^2}{\Omega^2} \sin^2\left(\frac{\Omega t}{2}\right),$$

while the corresponding time-dependent probability that the system will be found in the ground state takes the form $$|a_0(t)|^2 = 1 - |a_1(t)|^2 = 1 - \frac{\omega_R^2}{\Omega^2} \sin^2\left(\frac{\Omega t}{2}\right).$$

At resonance, $\Delta = 0$ and $\Omega = \omega_R$ so that in this case:

$$|a_1(t)|^2 = \sin^2\left(\frac{\omega_R t}{2}\right)$$

$$|a_0(t)|^2 = 1 - \sin^2\left(\frac{\omega_R t}{2}\right) = \cos^2\left(\frac{\omega_R t}{2}\right)$$

Accordingly, one physically significant consequence of the Rabi frequency is that the system is observed to be coherently cycled (i.e., no abrupt changes in the phases or amplitudes of the wavefunctions) between the ground and the excited states by the application of radiation. At resonance, the system is completely inverted after a time $$t_\pi = \frac{\pi}{\omega_R},$$

while off-resonance there is a reduced probability for finding the system in the excited state.

This simple description of a coherently driven system assumes the absence of decay processes, such as spontaneous emission of photons from an excited electronic state (i.e., fluorescence). Spontaneous emission of a photon generally breaks the coherence of the excitation and resets the system to the ground state (commonly referred to as a $T_1$ process). Similarly, collisions may also cause relaxation in the various energy manifolds of the system. In fact, collisions may reset the phase of the atomic or molecular wavefunction (only the relative phases of $\psi_1$ and $\psi_0$ generally being important) without changing any of the populations (commonly referred to as a $T_2$ process). These phase-changing collisions also interrupt coherent cycling of the system. Such processes were first studied in nuclear magnetic resonance (NMR) experiments and have subsequently been extensively studied in the field of quantum optics.

The effect of collisions and other relaxation phenomena is generally to dampen coherent cycling of the excited system (e.g., Rabi oscillations). However, Rabi oscillations may be observed in any quantum system simply by increasing the intensity of the radiation so that at some point the Rabi cycling frequency exceeds the relaxation frequency, $\omega_R \gg \omega_{relaxation}$, and coherent behavior will be observed to develop. This may easily be achieved, for example, in NMR experiments where spin relaxation processes are slow and many watts of radio frequency power may be applied to the system. In the infrared and visible region of the spectrum, relaxation processes are much faster and Rabi oscillations are normally dampened. For example, a real system would oscillate briefly when a strong field is applied suddenly to it, but quickly loses coherence and saturates. When the system is saturated, half of the molecules in the system are in the lower state and half are in the upper state. The rate of stimulated emission matches the rate of absorption.

The case of weak electromagnetic radiation, for example, interacting with the system is also common. In fact, before the development of the laser in 1960, the weak-field case was applied to all regions of the spectrum except in the radio-frequency and microwave regions, where powerful coherent sources were generally available. In the weak-field case, there is a negligible buildup of population in the excited state, so that $a_1 \approx 0$, $a_0 \approx 1$, wherein the time derivative becomes $$\dot{a}_1 = \frac{i\omega_R}{2}e^{-i\Delta t},$$

which may be readily integrated to yield:

$$a_1 = \frac{i\omega_R}{2}\int_0^t e^{-i\Delta t}$$
$$= \frac{\omega_R}{-2\Delta}(e^{-i\Delta t} - 1)$$

The probability for finding the system in the excited state after a time t is accordingly given by:

$$P_{0 \to 1} = |a_1|^2 = \frac{\omega_R^2}{\Delta^2}\sin^2\left(\frac{\Delta t}{2}\right) = \frac{\mu_{10}^2 E^2 \sin^2\left(\frac{(\omega - \omega_{10})t}{2}\right)}{\hbar^2(\omega - \omega_{10})^2}$$

which assumes monochromatic radiation and short interaction times; these requirements, of course, being inconsistent with one another due to the Heisenberg Uncertainty Principle as expressed by $\Delta E \Delta t \geq \hbar$ or $$\Delta \nu \Delta t \geq \frac{1}{2\pi}.$$

If monochromatic radiation is applied to the system for a time $\Delta t$, then the system "sees" radiation of width $$\Delta \nu = \frac{1}{2\pi \Delta t}$$

in frequency space; which certainly may not be understood as being monochromatic. For example, a pulse of radiation 10 ns in duration has an intrinsic width of at least 160 MHz in frequency space. Accordingly, before the transition probability expression may be used, the effects of the finite frequency spread of the radiation must be included.

Consider, for example, the radiation applied to the system as being broad band rather than monochromatic and having a radiation density $$\rho = \frac{\varepsilon_0 E^2}{2}.$$

The total transition probability is given by integrating over all frequencies:

$$P_{0 \to 1} = \frac{2\mu_{10}^2}{\varepsilon_0 \hbar^2} \int \rho_\upsilon(\omega) \frac{\sin^2\left(\frac{(\omega - \omega_{10})t}{2}\right)}{(\omega - \omega_{10})^2} d\omega$$
$$= \frac{2\mu_{10}^2}{\varepsilon_0 \hbar^2} \rho_\upsilon(\omega_{10}) \int \frac{\sin^2\left(\frac{(\omega - \omega_{10})t}{2}\right)}{(\omega - \omega_{10})^2} d\omega$$
$$= \frac{\mu_{10}^2}{\varepsilon_0 \hbar^2} \rho_\upsilon(\omega_{10}) \pi t$$

in which $\rho(\omega)$ is assumed to be slowly varying near $\omega_{10}$ so that it may be discarded from the integration. This is the case because $$\frac{\sin^2\left(\frac{(\omega - \omega_{10})t}{2}\right)}{(\omega - \omega_{10})^2}$$

is sharply peaked at $\omega = \omega_{10}$. The absorption rate per molecule is thus given by $$\frac{d}{dt}P_{0 \to 1} = \frac{\pi \mu_{10}^2}{\varepsilon_0 \hbar^2}\rho_\upsilon(\omega_{10}).$$

In order to derive an expression for the absorption coefficient in terms of the transition dipole moment, the immediately preceding equation may be compared with the previously derived expression $$\frac{d}{dt}N_1 = B_{0 \to 1}\rho_\upsilon(\upsilon_{10})N_0,$$

in which $N \approx N_0$ for the weak-field case. Dividing by N yields the transition probability per molecule $$\frac{d}{dt}\left(\frac{N_1}{N}\right) = \beta_{0 \to 1}\rho_\upsilon(\upsilon_{10}) \text{ or } \frac{d}{dt}P_{0 \to 1} = \beta_{0 \to 1}\rho_\upsilon(\upsilon_{10}).$$

A factor of three (3) is missing from $$\frac{d}{dt}P_{0 \to 1} = \frac{\pi \mu_{10}^2}{\varepsilon_0 \hbar^2}\rho_\upsilon(\omega_{10}) \text{ because } \frac{d}{dt}P_{0 \to 1} = \beta_{0 \to 1}\rho_\upsilon(\upsilon_{10})$$

has been derived using isotropic radiation traveling in the x, y and z directions, while $$\frac{d}{dt}P_{0\to 1} = \frac{\pi\mu_{10}^2}{\varepsilon_0\hbar^2}\rho_\upsilon(\omega_{10})$$

has been derived using a plane wave traveling along the z coordinate. Since only the z component of the isotropic radiation is considered effective in inducing a transition, and since $\rho(\upsilon)=2\pi\rho(\omega)$, the resulting expression becomes:

$$B_{0\to 1} = \frac{1}{6\varepsilon_0\hbar^2}\mu_{10}^2 = \frac{2\pi^2}{3\varepsilon_0\hbar^2}\mu_{10}^2 \text{ and } A_{1\to 0} = \frac{16\pi^3\upsilon^3}{3\varepsilon_0 hc^3}\mu_{10}^2.$$

These equations are significant results to the extent that they relate the observed macroscopic transition rates to the microscopic transition dipole moment of an atom or molecule. Upon substitution of the values of the constants, the following is obtained: $A_{1\to 0}=3.136\times 10^{-7}\upsilon^{18}\ {}^3\mu_{10}^2$, with $\upsilon^{-3}$ typically expressed in $cm^{-1}$ (e.g., wavenumbers) and $\mu_{10}^2$ in debye. Although these equations are essentially correct, one factor that has generally been neglected is the possibility of relaxation.

When the loses corresponding to collisions or the spontaneous radiative lifetime of an excited state are considered, the molecular absorption line shape changes from a Dirac delta function $\delta(\upsilon-\upsilon_{10})$ that is generally infinitely sharp and infinitely narrow (but with unit area) to a real molecular line shape. As described vide infra, the line shape function $g(\upsilon-\upsilon_{10})$ is typically either a Lorentzian or a Gaussian function with unit area but finite width and height in accordance with $$B_{0\to 1} = \frac{2\pi^2}{3\varepsilon_0\hbar^2}\mu_{10}^2 g(\upsilon-\upsilon_{10}) \text{ and } A_{1\to 0} = \frac{16\pi^3\upsilon^3}{3\varepsilon_0 hc^3}\mu_{10}^2 g(\upsilon-\upsilon_{10}),$$

where $\int B_{0\to 1}d\upsilon = B_{0\to 1}$ and $\int A_{1\to 0}d\upsilon = A_{1\to 0}$.

Thus a physical basis is described for the interaction of radiation with matter in accordance with various exemplary implementations of the present invention. The specific example of electromagnetic radiation has been used to representatively describe any endergonic (e.g., absorptive) processes and/or any exergonic (e.g., emissive) processes in, for example, a polyatomic molecular system. Skilled artisans will appreciate that other sources of radiation may be used in accordance with various other embodiments of the invention, such as, but not limited to: particle beam radiation, particle radiation (e.g., DeBroglie matter wave radiation), wave radiation, wave-packet radiation and/or any source of radiation now known or hereafter derived by those skilled in the art.

Fluorescence, Phosphorescence and Chemiluminescence

The spectroscopic methods of fluorescence, phosphorescence and chemiluminescence are generally referred to as "luminescence techniques". Fluorescence and phosphorescence are alike in that excitation generally occurs as a result of absorption of photons. As a consequence, fluorescence and phosphorescence are often referred to by the more general term "photoluminescence". Fluorescence differs from phosphorescence in that the electronic energy transitions do not typically involve a change in electron spin. Additionally, fluorescence is usually relatively short-lived with luminescence ceasing almost immediately (i.e., on the order of $<10^5$ seconds). Phosphorescence, on the other hand, involves a change in electron spin with luminescence typically enduring for a readily detectable time after termination of irradiated excitation—often several seconds or more. In most instances, photoluminescent emissions are generally longer in wavelength than the radiation used for the corresponding excitation.

The third type of luminescence, chemiluminescence, is based upon the emission spectrum of an excited species that is formed in the course of a chemical reaction. In some cases, the excited particles are the products of a reaction between the analyte and a suitable reagent (usually a strong oxidant such as ozone or hydrogen peroxide); the result is a spectrum characteristic of the oxidation product of the analyte rather than the analyte itself. In other cases, the analyte is not directly involved in the chemiluminescence reaction; instead, it is the quenching effect of the analyte on a chemiluminescence reaction that serves as the analytical detected parameter.

Measurement of the intensity of photoluminescence or chemiluminescence permits the quantitative determination of a variety of important inorganic and organic chemical species—often in trace amounts. In general, the number of fluorometric methods has been somewhat larger than the number of applications of phosphorescence and chemiluminescence techniques to date.

One of the most attractive features of luminescence methods is the inherent sensitivities corresponding to the techniques; with detection limits often being one to three orders of magnitude smaller than those encountered in, for example, absorption spectroscopy. Typical detection limits are in the parts-per-billion (ppb) range for conventional FF applications. Another advantage of photoluminescent methods is the ability to use large linear concentration ranges, which are often significantly greater than those encountered in, for example, absorption methods. Finally, the selectivity of luminescence procedures is often better than that of absorption methods. Conventional luminescence methods, however, are much less widely applicable than absorption methods because of the relatively limited number of chemical systems that may be made to demonstrate luminescence. See, for example, S. Schulman, *Molecular Luminescence Spectroscopy*, 1985, 1988; W. R. Seitz, *Treatise on Analytical Chemistry*, 1981; J. R. Lakowicz, *Principles of Fluorescence Spectroscopy*, 1983; and G. G. Guilbault, *Practical Fluorescence*, 1990.

Raman Scattering

When radiation passes through a transparent sample, the molecules present scatter a fraction of the beam in all directions. In 1928, C. V. Raman discovered that the wavelength of a small fraction of the scattered radiation differs from that of the incident beam and furthermore that the shift in wavelength depends upon the electrodynamic structure of the molecules responsible for the scattering. C. V. Raman was awarded the Nobel Prize in physics in 1930 for this discovery and his systematic investigation of it.

The theory of Raman scattering, which is generally well understood, demonstrates that the Raman phenomenon results from quantized vibrational changes similar to those that may be observed with infrared absorption spectroscopy. Thus, the difference in wavelength between the incident and scattered radiation corresponds to wavelengths in the mid-infrared region. Indeed, the Raman spectrum and infrared absorption spectrum for a given compound often resemble one another quite closely. There are, however, differences between compounds that demonstrate infrared active and those that are Raman active. For some analytical investigations, the infrared method is a superior technique; whereas for others, the Raman procedure produces more useful spectra.

An important advantage of Raman spectroscopy, however, lies in the fact that water generally does not cause interference; indeed, Raman spectra may be obtained from aqueous solutions. In addition, glass or quartz cells may be employed, thus avoiding the inconvenience of working with sodium chloride or other atmospherically unstable windows. Despite these advantages, Raman spectroscopy was not widely employed by chemists for structural studies until lasers became available in the 1960's, which made spectra substantially easier to obtain. One deterrent to the use of Raman spectroscopy, for example, was interference from sample fluorescence or impurities in the sample. This problem has generally been overcome with the advent of infrared laser sources and Fourier transform data analysis.

Raman spectra are typically obtained by irradiating samples with a powerful laser source of visible or infrared monochromatic radiation. During irradiation, the scattered radiation is measured at some angle (usually 90 degrees) with a suitably adapted spectrometer. The intensities of Raman lines are generally on the order of 0.001% of the intensity of the source; as a consequence, detection and measurement are often difficult. An exception to this is noted with resonance Raman spectroscopy.

Assuming a beam of radiation having a frequency $\upsilon_{ex}$ is incident upon a solution of an analyte, the electric field E of the radiation may be described by $E=E_0 \cos(2\pi\upsilon_{ex}t)$, where $E_0$ is the amplitude of the wave. When the electric field of the radiation interacts with the electron distribution of an analyte bond, it induces a dipole moment $\mu$ in the bond in accordance with $\mu = \xi E = \xi E_0 \cos(2\pi\upsilon_{ex}t)$, where $\xi$ is a proportionality constant called the polarizability. This constant is a measure of the deformability of the bond in an electric field.

In order for an analyte to be Raman active, the polarizability of a bond must vary as a function of the distance between nuclei according to the equation $$\xi = \xi_0 + (r - r_{eq})\left(\frac{\partial \xi}{\partial r}\right),$$

where $\xi_0$ is the polarizability of the bond at the equilibrium internuclear distance $r_{eq}$ and r is the internuclear separation. The change in internuclear separation $$\frac{dr}{dt}$$

varies with the frequency of the vibration $\upsilon_v$ according to $r - r_{eq} = r_m \cos(2\pi\upsilon_v t)$, where $r_m$ is the maximum internuclear separation relative to the equilibrium position. Accordingly, the following relation may be derived via substitution:

$$\xi = \xi_0 + \left(\frac{\partial \xi}{\partial r}\right) r_m \cos(2\pi\upsilon_v t).$$

Accordingly, an expression for the induced dipole moment $\mu$ may be derived as:

$$\mu = \xi_0 \cos(2\pi\upsilon_{ex}t) + E_0 r_m \left(\frac{\partial \xi}{dr}\right)\cos(2\pi\upsilon_v t)\cos(2\pi\upsilon_{ex}t).$$

Using the trigonometric identity $$\cos x \cos y = \frac{\cos(x+y) + \cos(x-y)}{2},$$

this expression becomes:

$$\mu = \xi_0 E_0 \cos(2\pi\upsilon_{ex}t) +$$
$$\frac{E_0}{2}r_m\left(\frac{\partial \xi}{\partial r}\right)\cos[2\pi(\upsilon_{ex}-\upsilon_v)t] + \frac{E_0}{2}r_m\left(\frac{\partial \xi}{\partial r}\right)\cos[2\pi(\upsilon_{ex}+\upsilon_v)t]$$

The first term in this equation $\xi_0 E_0 \cos(2\pi\upsilon_{ex}t)$ represents Rayleigh scattering, which occurs at the excitation frequency $\upsilon_{ex}$. The second term $$\frac{E_0}{2}r_m\left(\frac{\partial \xi}{\partial r}\right)\cos[2\pi(\upsilon_{ex}-\upsilon_v)t]$$

and third term $$\frac{E_0}{2}r_m\left(\frac{\partial \xi}{\partial r}\right)\cos[2\pi(\upsilon_{ex}+\upsilon_v)t]$$

correspond to the Stokes and anti-Stokes frequencies $(\upsilon_{ex}-\upsilon_v)$ and $(\upsilon_{ex}+\upsilon_v)$ respectively; wherein the excitation frequency has been modulated by the vibrational frequency of the bond. It is important to note that Raman scattering requires that the polarizability of a bond vary as a function of distance $$\left(\text{e.g., } \frac{\partial \xi}{\partial r} \neq 0\right).$$

The differences between Raman and infrared spectra are not surprising when it is considered that the mechanisms, although generally dependent upon substantially the same vibrational modes, arise from processes that are mechanistically different. Infrared absorption, for example, requires that a vibrational mode of the molecule have a change in dipole or charge distribution associated with it—only then may resonantly tuned radiation interact with the molecule to promote it into an excited vibrational state. In contrast, scattering involves a momentary distortion of the electrons distributed around a bond in a molecule followed by radiative relaxation as the bond returns to the ground state. In an electronically distorted configuration, the molecule is temporarily polarized; that is, the molecule develops a momentarily induced net dipole. Because of this fundamental mechanistic difference, the Raman activity of a given vibrational mode may generally differ substantially from its corresponding infrared activity. For example, a homonuclear molecule such as molecular nitrogen, has no net dipole moment either in its equilibrium position or when engaged in a stretching vibrational mode. Thus, based on the selection rules, absorption of radiation for this vibrational mode and frequency generally is not observed to occur. On the other hand, the polarizability of the bond between the two atoms varies periodically in phase with the stretching vibration; reaching a maximum at the greatest separation and a minimum at closest approach. A Raman shift corresponding in frequency to the vibrational mode accordingly results.

As used herein, the term "Raman spectroscopy" may be understood to include Raman scattering, Rayleigh scattering, resonance Raman spectroscopy, surface-enhanced Raman spectroscopy (SERS) and nonlinear Raman spectroscopy as well. For further description of the theory and practice of induced polarization scattering and spectroscopy, see, for example: N. B. Colthup et al., Introduction to Infrared and Raman Spectroscopy, 1990; P. Hendra et al., Fourier Transform Raman Spectroscopy:

Instrumental and Chemical Applications, 1991; J. G. Grasselli et al., Chemical Applications of Raman Spectroscopy, 1981.

Near-field Transform Spectroscopy

The present invention provides a system and method for transform spectroscopic detection of sub-diffraction-limited scale phenomena. In one exemplary embodiment, a system comprising a source of radiation, a near-field aperture array, a chromatographic flow field, a detector and a data processor is disclosed. In accordance with various exemplary embodiments of the invention, the data processor is configured to transform time-domain signal input into frequency-domain output to achieve inter alia sub-diffraction-limited scale discrimination of at least one chromatographically separated analyte within a heterogeneous multi-component sample. Other representative embodiments of the present invention also provide for a novel regime of analyte-specific detection by exploiting higher frequency information in the localized region of non-propagative evanescent fields.

Figure 3:
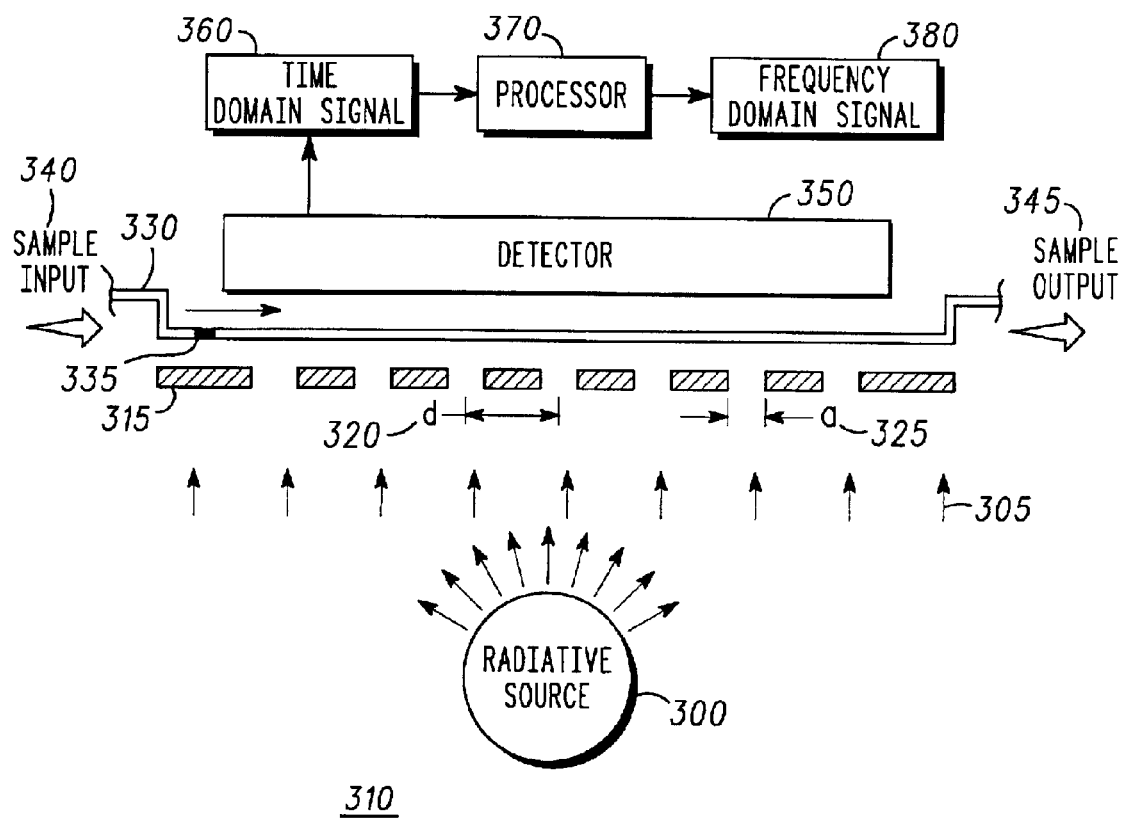
FIG. 3 illustrates a schematic view of an exemplary near-field array detection system in accordance with one embodiment of the present invention.

An exemplary embodiment of the present invention includes a detection system, as representatively illustrated for example in FIG. 3, employing a near-field aperture array 315. System 310 demonstrates the capacity to differentiate inter alia a single analyte component from a heterogeneous multi-component sample 335.

Sample 335 is loaded onto chromatographic field 330 at sample input port 340. Chromatographic field 330 may be a packed column, an open-tubular column, a capillary surface coated with chromatographic stationary phase media or any other type of chromatographic apparatus now known or hereafter derived by those skilled in the art. Various mobile phase solvents may be used to transport sample 335 through the chromatographic field 330; for example, any fluid, including: any gas; any liquid; any plasma; and/or any supercritical fluid or any mobile phase and/or solvent system now known or hereafter derived in the art. Various chromatographic methods may be employed, such as, for example, adsorption, partition, ion-exchange, molecular exclusion and/or affinity chromatography and such other methods now known or hereafter developed in the art. Additionally, various methods for calibrating or otherwise monitoring peak asymmetry, plate height and/or capacity factors, either now known or hereafter derived in the art, may be optionally used. For purposes of the instant disclosure, "peak asymmetry" may be understood to include inter alia baseline drift, peak broadening, sample overloading, tailing, and/or the like.

Sample 335 moves through chromatographic field 330 to exit at sample output port 345. As sample 335 traverses the sample flow path of chromatographic field 330, at least one component analyte of the sample 335 begins to separate in accordance with its specific mobility. Various factors that may contribute to the value of any given analyte's specific mobility may include, for example: the analyte's equilibrium between the stationary and mobile phases; the number of theoretical plates; plate height; the mechanism of stationary phase adsorption; non-uniform porosity; anisotropic transport; hydrophilicity/hydrophobicity; capillary defects; chromatographic field design; column diameter; column volume; solvent flow rate; back pressure; and/or temperature or such other parameters now known or hereafter developed or otherwise described in the art.

Additionally, sample 335 may be any of, for example: an isotropic sample; an anisotropic sample; a substantially homogeneous sample; a substantially heterogeneous sample; a multi-component sample; and/or a standard or calibration sample or any sample suitably adapted for flow-path transport in accordance with various exemplary embodiments of the present invention now known or hereafter developed in the art.

Radiative source 300 is provided for subsequent generation of near-field regions. Radiative source 300 may include any type of energy source such as, for example: electromagnetic radiation; monochromatic radiation; polychromatic radiation; polarized radiation; circularly-polarized radiation; coherent radiation; incoherent radiation; a particle beam; visible light; ultraviolet light; infrared light; radio waves; microwaves; x-rays and gamma rays or any other form of energy now known or hereafter derived or otherwise discovered in the art.

In an exemplary embodiment in accordance with the present invention, aperture field 315 (e.g., aperture array) is disposed between radiative source 300 and chromatographic field 330. Aperture array 315 generally comprises apertures 325 having dimension a with aperture spacing d 320. For effective generation of near-field regions, said dimension a is generally selected as effectively below the diffraction limit of said radiative source 300 (e.g., less than the wavelength $\lambda$ of incident radiation 305). In a representative application, exposure of said aperture field 315 with incident radiation 305 generates evanescent fields at regions in close proximity to apertures 325 on the opposing side of aperture field 315. A chromatographic field 330 is positioned in effective proximity to the sample transport flow-path so as to intersect with the evanescent field regions generated by near-field apertures 325. In general, the sample flow-path is aligned or otherwise oriented so that the sample transport vector is substantially aligned with the aperture field vector corresponding to the intersection of multiple evanescent field regions. In this way, the sample flow path may be said to be suitably adapted for moving the sample and/or component analytes substantially along the aperture field 315 in effective near-field proximity to said aperture field. In various other exemplary embodiments of the invention, the sample flow-path may optionally not include a chromatographic field 330, but instead a path for sample 335 to traverse aperture field 315 without substantial adsorption or retention. Additionally, sample flow-path may comprise fluidic channels comprising, for example, micro-fluidic and/or nano-fluidic dimensions.

In various exemplary and representative embodiments of the present invention, apertures 325 may comprise openings having any geometry, such as, for example: circular openings; oval openings; slit openings; openings of regular geometry; openings of irregular geometry and/or any aperture geometry now known or hereafter derived by those skilled in the art. Aperture spacings 320 may comprise uniformly spaced intervals. In other exemplary embodiments, aperture spacings 320 may alternatively, conjunctively or sequentially comprise functionally and/or parametrically spaced intervals for which the functions and/or parameters for determining the spacing intervals are known or otherwise capable of being determined. In still other embodiments, aperture spacings 320 may comprise various other aperture spacing configurations and/or methods now known or hereafter derived in the art.

Additionally, aperture array performance may be optionally enhanced by combining, for example, surface plasmon assisted elements so as to constructively scatter at least a portion of incident radiation 305 into said apertures 325. In one exemplary embodiment, plasmon assisted enhancement may be generated, for example, by an array of small indentations or other surface morphology on the surface of incidence of aperture field 315 in effective proximity to apertures 325 so as to effectively scatter radiation 305 that would have not entered or otherwise interacted with apertures 325 under normal incidence from source 300. Any plasmon morphology and/or geometry capable of inducing radiative scattering now known or hereafter developed in the art may be alternatively, conjunctively or sequentially used for plasmon assisted enhancement. For a discussion of plasmon assisted enhancement of transmission through diffraction gratings via radiation coupling, see, for example, Ebbesen et al., *Nature,* 391, 667, 1998.

Detector 350 is positioned in effective proximity to detect signal substantially originating from a region corresponding to the intersection of said sample flow-path with the evanescent fields of aperture array 315. In various exemplary embodiments, detector 350 may be any input transducer device suitably adapted to convert one type of energy or signal to another; for example: a thermocouple; a photocell; a photomultiplier (i.e., PMT, APD, CCD, etc.); electrodes; glass-calomel electrodes; and/or photographic film or any other detection device and/or method now known or hereafter derived in the art. In various representative aspects in accordance with exemplary embodiments of the present invention, detector 350 is adapted to demonstrate effective response and/or sensitivity to, for example: a quantum state transition; a meta-stable atomic state transition (i.e., radioactive decay processes); a nuclear spin-state transition (i.e., NMR); an electronic spin-state transition (i.e., phosphorescence); an electronic state transition (i.e., fluorescence, chemiluminescence, Auger processes, etc.); a rotational state transition; a vibrational state transition (Raman scattering, Rayleigh scattering, etc.); a biomolecular interaction; a kinetic rate constant; a chromatographic mobility; an index of refraction; magnetization; and a magnetic susceptibility or any other physical and/or chemical property now known or hereafter developed or otherwise discovered in the art. Additionally, detected analytes for sample 335 may include any of, for example: an atom; a molecule; a molecular reporter; a biomolecule; a biomolecular reporter; a luminescence tag; a fluorescence tag; a phosphorescence tag; a chemiluminescence tag; a magnetic tag; a magnetization tag; a radioactive tag; a nuclear spin-state tag; a chemical reagent; a chemical precursor and/or a nanoprobe or such other detection targets now known or hereafter developed or otherwise discovered in the art.

Detector 350 provides a time-domain signal 360 to data processor 370 for subsequent analysis. Acquired signal 360 may correspond to any chemical and/or physical property of various analyte components and may also be acquired by affirmative analyte-specific generation of said acquired signal 360 and/or an analyte-quenched signal. In the case of quenched signal detection, analyte-specific information may be obtained, for example, by comparison of a background signal with the analyte-quenched signal in accordance with various systems and/or methods now known or hereafter derived in the art.

Processor 370 receives time-domain signal data 360 as input and produces frequency-domain signal data 380 output. In a representative and exemplary embodiment, processor 370 converts time-domain data 360 into frequency-domain data 380 by operation of, for example, a Fourier transformation (FT); however, any transformation, such as, for example: a fast Fourier transformation (FFT); a Laplace transformation; a Hankel transformation; a Mellin transformation; a Hadamard transformation; and/or a Hilbert transformation or any transformation now known or hereafter derived in the art may be used alternatively, conjunctively or sequentially to produce frequency-domain output from time-domain input.

Processor 370 may be any of, for example: a special purpose processor; a multi-purpose processor; a solid-state circuit; an integrated circuit; a digital data processor; a digital computer; a personal computer; a mainframe computer; a workstation computer; a distributed computing network; an integrated analytical device; a portable analytical device; a hand-held analytical device; a stand-alone analytical device; and/or a multi-purpose analytical instrument or such other processing systems now known or hereafter derived by those skilled in the art. Additionally, processor 370 may operate by data analysis means including any of, for example: ROM software; RAM software; a compiled program; an interpreted program; a runtime library call; a dynamic link library call; a subroutine call; a call to an external executable program; an operating system class call; a database query; a programming applet and/or a programming script or such other data analysis methods now known or hereafter developed in the art.

In other representative and exemplary embodiments, in accordance with the instant invention, various apertureless techniques for the generation of NF zones may also be used. For example, nanometric particles may be immersed in optical NF zones near a sample surface where NF energy is scattered into propagative wave components that may be subsequently detected in the FF. In various exemplary embodiments, nanoparticles deposited very near or even in contact with the sample surface may be considered to comprise plasmons. Accordingly, the geometry, morphology and chemical or electronic properties of the nanoparticles may be suitably adapted inter alia to control or otherwise modify the magnitude of scattering.

Moreover, nanometric particles may be alternatively, conjunctively or sequentially employed to operate as, for example, localized antennas for generation of nanometric evanescent fields with which the sample may suitably interact to effect inter alia analyte detection. Various other apertureless techniques may also be employed, such as, for example: SAIM; apertureless AFM; and apertureless SNOM or such other apertureless NF techniques now known or hereafter developed or otherwise described in the art. Accordingly, those skilled in the art will appreciate that while the embodiment representatively illustrated in FIG. 3 depicts a system and method of NF transform spectroscopic analysis operating in a transmission mode, various other embodiments of the present invention may be readily adapted to any configuration or design for operation in an absorptive, reflective and/or scattered reflectance mode.

Figure 4:
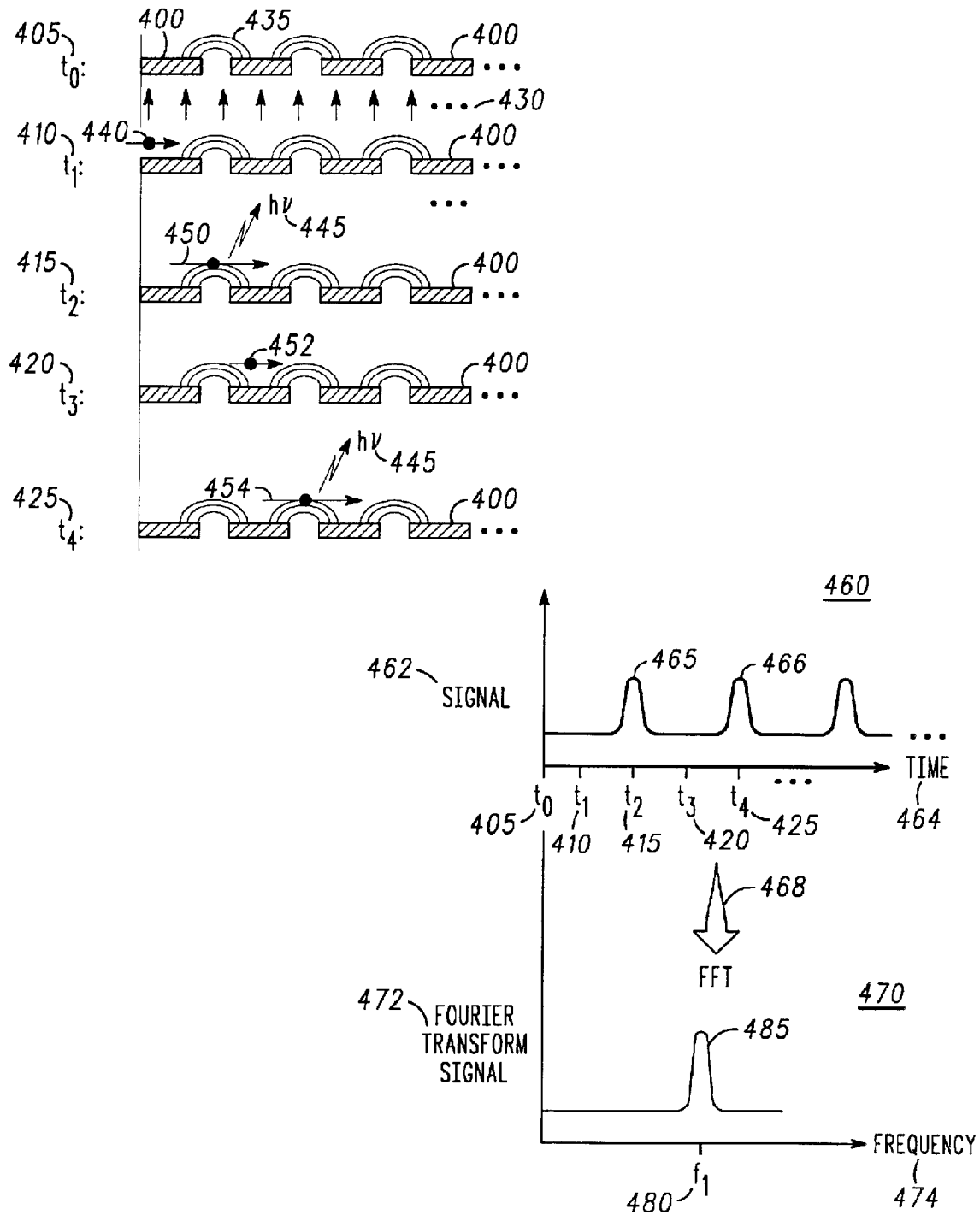
FIG. 4 illustrates an exemplary process for the collection of near-field, time-domain data for subsequent transformation to near-field, frequency-domain data in accordance with another representative embodiment of the present invention.

A representative process and method, in accordance with one exemplary embodiment of the invention, is depicted, for example, in FIG. 4 for the collection of near-field, time-domain data 460 for subsequent transformation 468 to near-field, frequency-domain data 470. Near-field aperture array 400 is exposed to incident radiation 430 to generate evanescent field regions 435. At time $t_0$ 405, no sample loading has yet occurred. Between time $t_0$ 405 and time $t_1$ 410, sample 335 is loaded onto chromatographic field 330 and at least one analyte component 440 begins to move through the sample flow-path along the aperture field 400. At time $t_2$ 415, analyte component 440 enters a near-field zone 435 where analyte 440 is excited and subsequently produces, for example, a photon of energy hυ 445 (i.e., fluorescence). Photon 445 may thereafter be detected by detector 350 to produce a signal 465 indexed at time $t_2$ 415, as shown, for example, in time-domain chromatogram 460. At time $t_3$ 420, analyte particle 440 enters an area between near-field zones 435 such that no excitation occurs and signal, therefore, is generally not produced. As analyte 440 continues to flow through sample flow-path of chromatographic field 330, analyte 440 enters another near-field region 435 at time $t_4$ 425 to produce a correspondingly indexed signal 466 as shown in the time-domain chromatogram. This process continues to occur over the length of the sample flow-path and/or near-field aperture array until the sample traverses the detection region. Accordingly, the time-domain chromatogram 460 provides signal data 462 (e.g., the ordinate) as a function of time index 464 (e.g., the abscissa) which is characteristic for the sample—in this case, a sample comprised of a single analyte 440. After performing a fast Fourier transform 468 on the time-domain data 460, a frequency-domain plot 470 is obtained wherein the Fourier signal 472 is given as a function of frequency 474. Accordingly, frequency $f_1$ 480 corresponds to Fourier signal 485 representing the "blink frequency" of analyte 440 as it moves through the detection field.

Figure 5:
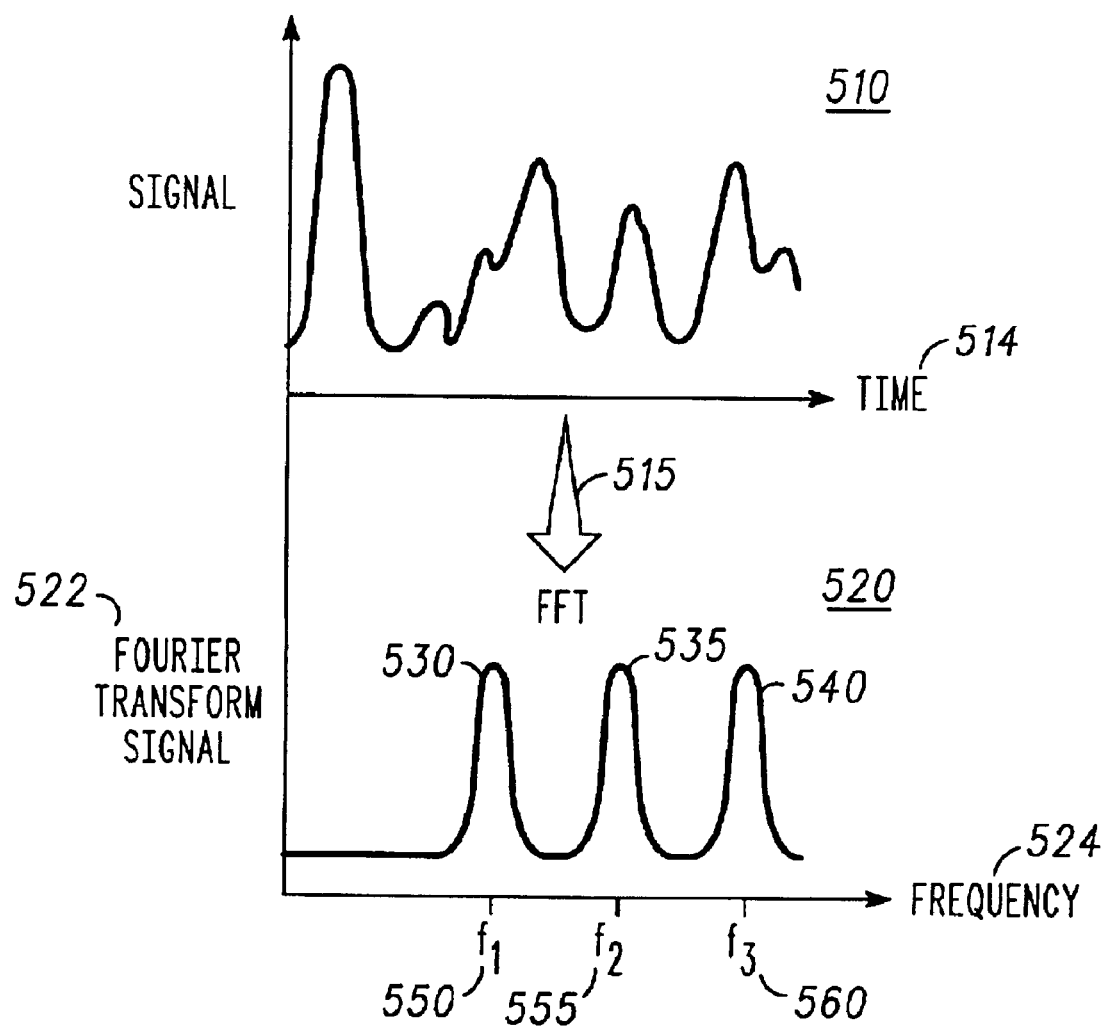
FIG. 5 illustrates transformation of representative multi-component analyte near-field, time-domain data into frequency-domain data in accordance with another exemplary embodiment of the present invention.

For multi-component samples, as generally depicted in FIG. 5, the time-domain chromatographic signal data 510 may be substantially more complex. In one exemplary embodiment, the chromatographic separation of a multi-component sample may be continuously interrogated at a number of evenly spaced intervals along the chromatographic field simultaneously by a single detector, such that the resulting signal trace represent the summation of analyte signals measured from interval points along the detection field. Over the course of the chromatographic separation, each analyte band progresses along the chromatographic field at an analyte-specific velocity to produce a series of evenly spaced Gaussian peaks; wherein, the detection signal trace comprises the accumulation of these several n Gaussian peaks for n analytes. Accordingly, the detection signal trace represents the time-domain chromatogram, which may be considered as a Shah convolution of the point detection function.

A Shah function I(x) is generally given as an infinite sequence of unit Dirac delta function impulses δ(x) spaced at unit intervals in accordance with $$I(x) = \sum_{n=-\infty}^{\infty} \delta(x-n).$$

A Fourier transformation may be employed to transform the time-domain signal into the frequency domain and will thus reveal the frequency components embedded in the time-domain signal data. Upon application of a Fourier transformation to the time-domain chromatogram, a frequency-domain plot is obtained in which each individual series of Gaussian peaks (convolved in the time domain) produces a characteristic frequency peak. De-convolution of the chromatogram 510 via FFT 515 to produce Fourier signal trace 520, for example, reveals three analyte frequencies $f_1$ 550, $f_2$ 555 and $f_3$ 560 corresponding to three Fourier de-convolved transform signals 530, 535 and 540 respectively.

Figure 6:
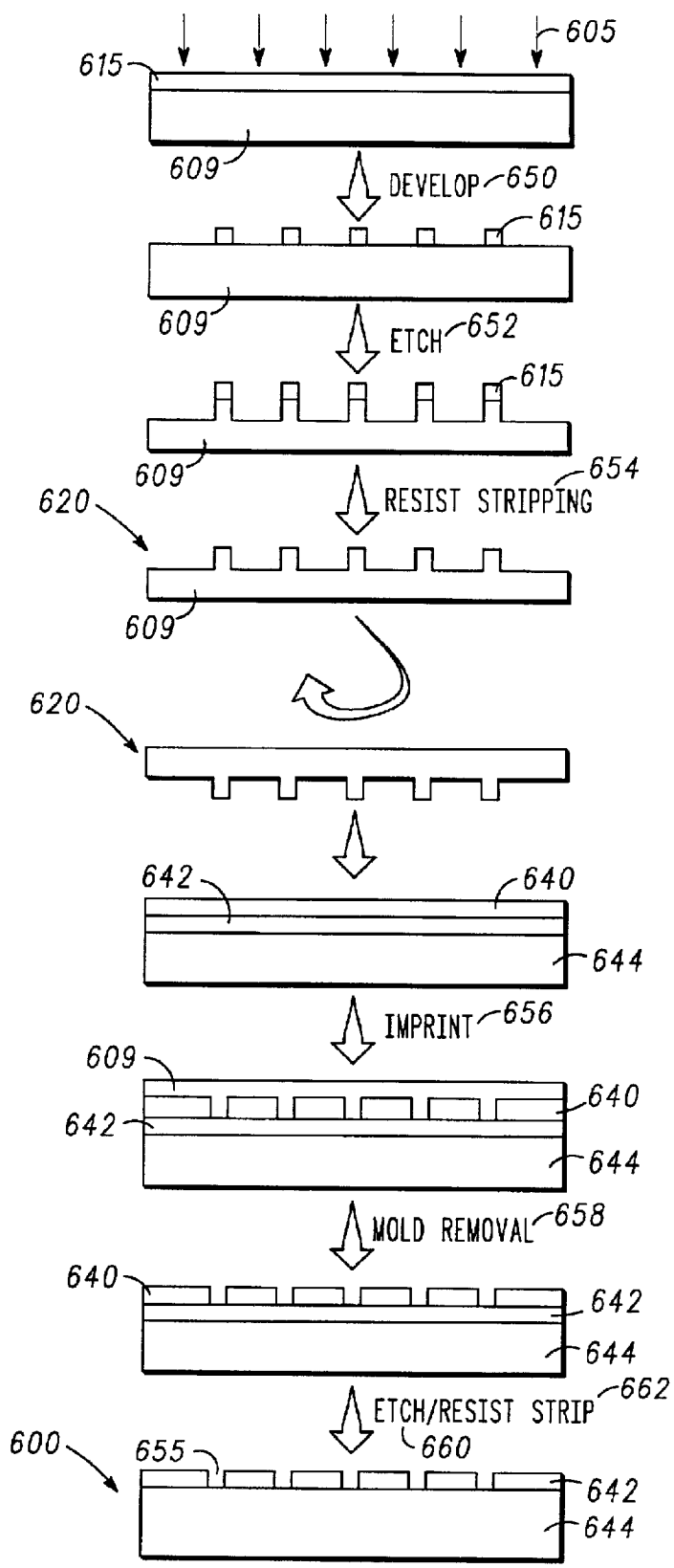
FIG. 6 illustrates an exemplary process for the production of a channel array system in accordance with another representative embodiment of the present invention.

In accordance with another exemplary embodiment of the present invention, a near-field aperture array may be defined by, for example, e-beam lithography on an aluminum film deposited on a quartz (e.g., silicon) substrate. Alternatively, a near-field aperture array may be suitably fabricated by nanoimprint lithography, as representatively illustrated, for example, in FIG. 6. An aperture array master mold 620 is generally formed by deposition of PMMA 615 (or other suitably adapted negative resist) on, for example, a silicon substrate 609 followed by e-beam writing 605, development 650, etching 652 and resist stripping 654 to produce an aperture master mold 620 having negative imprint features corresponding to the desired aperture specifications and tolerances. Thereafter, aperture master mold 620 may be engaged with an imprint die comprising a PMMA (or other negative resist) layer 640 deposited on aluminum 642 over silicon 644. Master mold 620 imprints 656 the aperture field features into the PMMA layer 640 which, after mold removal 658, etching 660 and resist stripping 662 yields aluminum aperture array 600 with apertures 655 defined therein.

Figure 7:
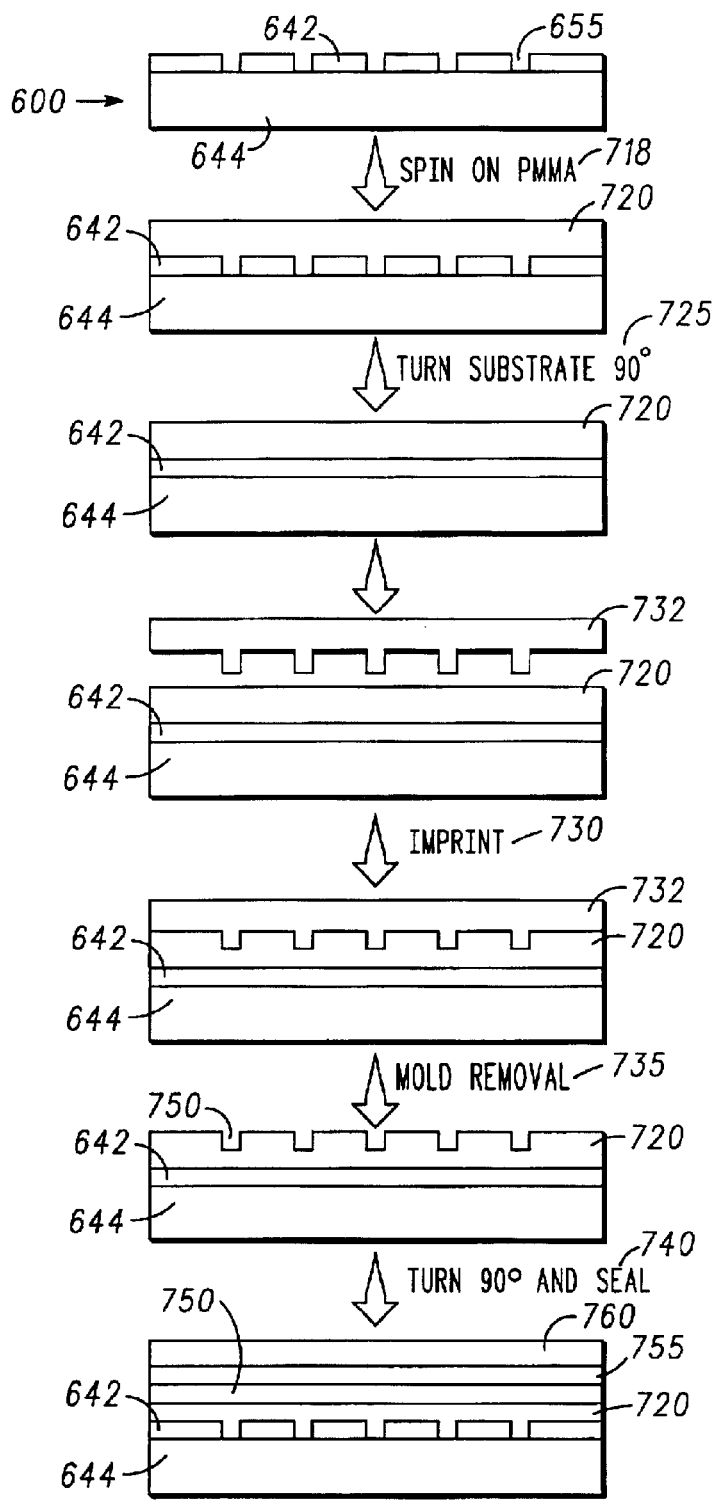
FIG. 7 illustrates an exemplary process for the production of an aperture array system in accordance with yet another representative embodiment of the present invention.

In another exemplary embodiment, sample flow-path channels may be e-beam defined in PECVD oxide coated on a metal film then sealed against, for example, a silicone-coated coverslip. Alternatively, fluidic channels may be suitably fabricated by nanoimprint lithography, as representatively illustrated in FIG. 7. Aperture array 600 is spin-coated 718 with PMMA 720 (or other suitably adapted negative resist). The composite substrate is then rotated 90 degrees 725 and then imprinted 730 with channel array master mold 732 in order to define fluidic channels comprising sample flow-path features corresponding to the desired specifications and tolerances. Thereafter, the mold 732 is removed, exposing fluidic channels 750, and the composite substrate is then rotated 90 degrees and sealed 740. In an exemplary embodiment, fluidic channels 750 may be sealed with a PDMS layer 755 and/or a coverslide 760.

Figure 8:
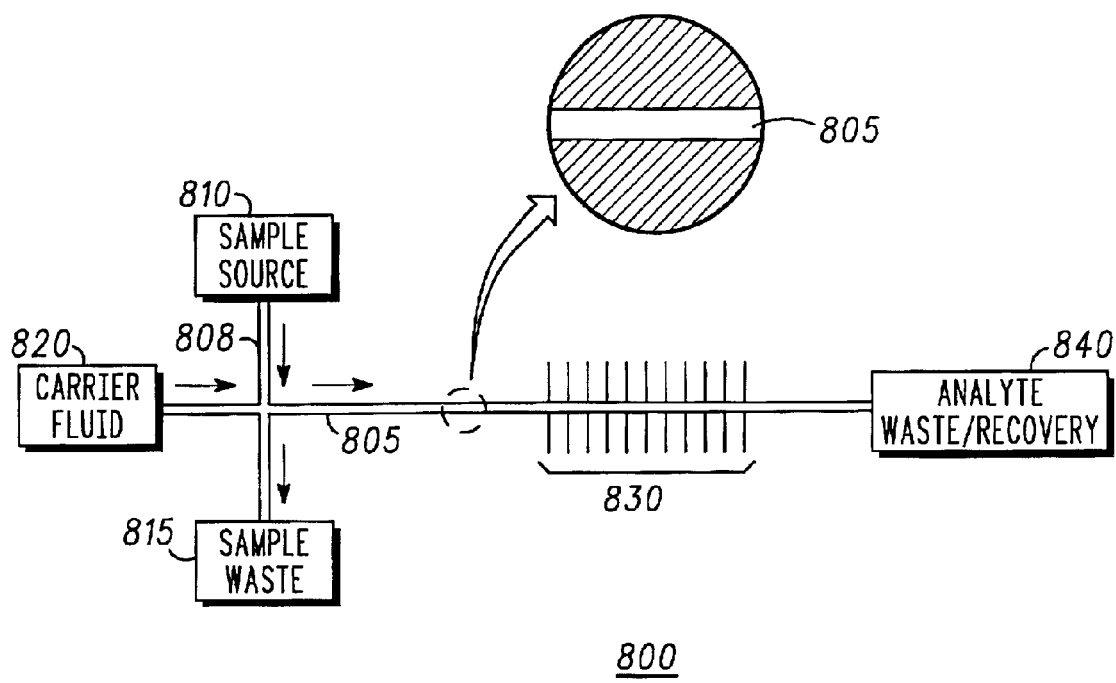
FIG. 8 illustrates a schematic of an exemplary system and method for sample loading and recovery in accordance with still another representative embodiment of the present invention.

FIG. 8 illustrates a process schematic of a system and method for sample loading and analyte reclamation in accordance with another exemplary embodiment of the present invention. Sample transport path 808, from sample source 810 to sample waste 815, is oriented substantially perpendicular to analyte flow-path 805. Carrier fluid 820 (e.g., mobile phase solvent) mixes with sample at the intersection of sample transport path 808 and analyte flow-path 805. Analyte flow-path 805 may be suitably adapted to also function as a chromatographic field for the separation of analytes moving toward and through near-field aperture array 830. After detection, analytes may thereafter be recovered and/or processed as waste 840.

The present invention may be readily multiplexed for parallel processing of samples and may also be optionally implemented with cyclic chromatography to increase resolution in conjunction with faster separations without requiring pre-conditioning of the initial starting conditions at the time of sample loading. The disclosed system and method may also be optionally coupled with, for example, DNA micro-arrays and on-chip light sources (i.e., micro-hollow cathode plasma discharge elements). In one representative aspect, the present invention may further embody an integrated module for real-time monitoring and quantification of, for example: biomolecular reporters; chemical, luminescent, and/or magnetic tags, etc.; nucleic acid concentrations, PCR kinetics, flow-velocity measurements, analyte mobilities and various epigenomic applications and the like.

Representative advantages of NF transform spectroscopy may include, for example: improvement of S/N corresponding to enhanced spectroscopic resolution; further improvement of S/N with back-illuminated near-field excitation; higher spatial resolution defined by, for example, near-field apertures; no requirements for pre-determined control of the initial starting conditions for sample loading; ease of use; increased sample throughput with the utilization of multiplex detection and signal transform analysis; and the capability of single-molecule detection. Accordingly, the present invention may be employed to obtain novel information about, for example, a biochemical compound by exploiting higher frequency information of non-propagating evanescent fields and is more preferable for high-throughput applications than conventional NF methods employing scanning probes (i.e., AFM, NSOM, etc.) over immobilized samples. Additionally, frequency-domain signals have been observed to be generally proportional to analyte velocity distributions where the physical spacing of the apertures (e.g., the pitch) is fixed. Thus the disclosed system and method may also serve as an in situ self-calibrated velocitometer which may be effectively employed for evaluating, for example, various analyte mobilities.

In another exemplary application, a chromatographic field in accordance with a representative embodiment of present invention may including coating of the walls of the sample flow-path and/or aperture array with, for example, a photoliminescent polymer into which DNA capture probes or other suitable chemical ligands may be functionally grafted. Accordingly, when a DNA molecule flows through the sample flow-path, the DNA would bind to the capture probe thus affecting separation that may be detected, for example, via a change in an index of refraction and/or the scattering of radiation. Moreover, this type of chemical analysis may be extended beyond DNA applications to any ligand, intercalation, chelation or chemical binding system, method or process now known or hereafter developed or otherwise described in the art. Additionally, such a chemical binding system and/or method may be suitably adapted to provide for inter alia molecular data storage and/or detection.

Near-field Transform Monitoring of Chemical Polishing

Many electronic and computer-related products (i.e., semiconductors, CD-ROMs, computer hard disks, etc.) require highly polished surfaces in order to achieve optimum operational characteristics. Recent growth in the implementation of integrated circuit devices has generally resulted in a corresponding increase in demand for semiconductor wafers from which integrated circuit chips (IC's) may be fabricated. The need for higher density IC's, as well as the need for higher production throughput of IC's on a per-wafer basis, has resulted in a need for increasing the planarity of semiconductor wafer surfaces both during initial production of semiconductor wafers as well as during the actual fabrication of an IC on the wafer surface.

The production of IC's generally begins with the creation of high-quality semiconductor wafers. During the IC fabrication process, the wafers typically undergo multiple deposition, masking and etching process steps. After each deposition, a layer may be etched to create circuit component features. Because of the high precision required in the manufacturing of IC's, an extremely planar surface is generally needed on at least one side of a semiconductor wafer to ensure proper accuracy and performance of the microelectronic structures created at the wafer surface.

As multiple circuit layers are iteratively exposed and developed, the outermost surface of the substrate becomes increasingly non-planar. This occurs because the distance between the outer surface and the underlying substrate is greatest in regions of the wafer substrate where the least lithographic etching has occurred, and least in regions where the greatest etching has occurred. With a single circuit-pattern layer, these surface variations comprise a series of peaks and valleys where the vertical differential between the highest peak and lowest valley may be on the order of several thousand Angstroms. With the construction of multiple circuit layers, this vertical differential accumulates and becomes increasingly divergent—reaching several microns and perhaps eventually resulting in the production of defective IC devices.

In general the need for highly planar wafer surfaces becomes increasingly important as the size of the IC's decrease and the number of microstructures per IC increase. In order to manufacture ultra-high density IC's, chemical mechanical planarization (CMP) processes are generally employed to provide a suitably adapted surface that is both highly planar and uniform across substantially the entire surface of the wafer.

An exemplary wafer substrate for lithographic etching of circuit patterns may be constructed by coating, for example, a circular, flat, silicon wafer with a film of metal such as aluminum. A layer of photoresist may then be placed over the metal layer. Thereafter, a photolithographic apparatus is typically employed to expose the photoresist to electromagnetic or particle-beam radiation to produce a patterned photoresist layer. Exposed portions of the metal layer are then chemically etched leaving behind circuit component features. The remaining photoresist is then removed to permit further wafer processing. A second layer of circuit componentry may then be created, for example, by depositing an insulative layer (i.e., silicon dioxide) over the previously developed circuit features. The outer surface of the second insulative layer topologically conforms to the variations created by the etching of the underlying circuit pattern. This creates a series of peaks and valleys on the outermost surface of the second (e.g., insulative) layer. The resulting complexity and variation of topological features tends to increase with the exposure and etching of multiple component layers.

Photolithographic techniques used to pattern the photoresist typically have a depth of focus of about 0.2 to 0.4 microns for sub-half-micron features. If the photoresist layer is sufficiently non-planar (e.g., if the maximum vertical differential of any peak and any valley on the outer surface is greater than the depth of focus of the imaging device), then it generally may not be possible to properly focus the image onto the wafer to create the pattern for the next layer of componentry. Even where the imaging apparatus may be adapted to accommodate for the non-planarity created by any single patterned layer within the range of the device's depth of focus, after the deposition of a sufficient number of circuit layers, the maximum vertical differential will eventually exceed the imaging apparatus' depth of focus and, therefore, compromise its ability to accommodate for the non-planarity.

CMP machines have been developed to polish or planarize silicon wafer surfaces to the flat condition desired for manufacture of various IC components and the like. For a general discussion of conventional CMP processes and devices, see, for example: U.S. Pat. No. 4,805,348, issued in February 1989 to Arai et al.; U.S. Pat. No. 4,811,522, issued in March 1989 to Gill; U.S. Pat. No. 5,099,614, issued in march 1992 to Arai et al.; U.S. Pat. No. 5,329,732, issued in July 1994 to Karlsrud et al.; U.S. Pat. No. 5,476,890, issued in December 1995 to Masayoshi et al.; U.S. Pat. Nos. 5,498,196 and 5,498,199, both issued in March 1996 to Karlsrud et al.; U.S. Pat. No. 5,558,568, issued in September 1996 to Talieh et al.; and U.S. Pat. No. 5,584,751, issued in December 1996 to Kobayashi et al.

Chemical mechanical polishing or planarizing of a surface of an object may be desirable for several reasons. For example, chemical mechanical polishing is often used in the formation of microelectronic devices to provide a substantially smooth, planar surface suitable for subsequent fabrication processes such as photoresist coating and pattern definition. Chemical mechanical polishing may also be used to form microelectronic features. For example, a conductive feature such as a metal line or a conductive plug may be formed on a surface of a wafer by forming trenches and vias on the wafer surface, depositing conductive material over the wafer surface and into the trenches and vias, and removing the conductive material on the surface of the wafer using chemical mechanical polishing, leaving the vias and trenches filled with the conductive material.

A typical chemical mechanical polishing apparatus suitable for planarizing the semiconductor surface generally includes: a wafer carrier configured to support, guide, and apply pressure to a wafer during the polishing process; a polishing chemistry such as a slurry containing abrasive particles and chemicals to assist removal of material from the surface of the wafer; and a polishing surface such as a polishing pad. In addition, the polishing apparatus may include an integrated wafer cleaning system and/or an automated load and unload station to facilitate automatic processing of wafers and/or component dies.

In an exemplary conventional CMP polishing method, one side of a silicon wafer is attached to a flat surface of a wafer carrier or chuck with the other side of the wafer pressed against a flat polishing pad. In general, the exposed surface of the pad incorporates an abrasive such as, for example, cerium oxide, aluminum oxide, fumed/precipitated silica, or other particulate abrasives, while the underlying support material may be formed of various commercially available compositions such as, for example, a blown polyurethane (i.e., the IC, SUBA IV and GS series of polishing pads generally available from Rodel Products, Scottsdale, Ariz., USA) or such other materials that are well known in the art.

During the polishing or planarization process, the workpiece (e.g., wafer) is typically pressed against the polishing pad surface while the pad rotates about its principle axis in the presence of a polishing chemistry. In particular, the wafer is placed in the carrier such that the surface to be polished is typically placed in contact with the polishing surface. The wafer is generally moved relative to the polishing surface while slurry is supplied to the area between the wafer and the polishing surface. Additionally, in order to improve polishing effectiveness, the wafer may also be rotated about its principal axis and oscillated over both the inner and outer radial surfaces of the polishing pad. The hardness and density of the polishing pad depends on the material comprising the workpiece to be polished and the degree of precision required in the polishing process.

CMP is a fairly complex process that differs substantially from simple wet sanding. In the CMP process, polishing slurry (i.e., an abrasive and at least one chemically reactive agent) is generally spread on the polishing pad to provide an abrasive chemical solution at the interface between the pad and wafer substrate. At least one chemically reactive agent in the slurry reacts with the outer surface of the substrate to form reactive sites. The interaction of the polishing pad and abrasive particles with the reactive sites results in polishing of the wafer substrate—that is to say, chemical mechanical planarization (or polishing) occurs when pressure is applied between the polishing pad and the workpiece being polished where the mechanical stresses and the abrasive particles within the slurry create mechanical strain on the chemical bonds on or near the surface being polished, rendering the chemical bonds more susceptible to chemical attack or corrosion (e.g., stress corrosion).

After the mechanical stresses weaken the chemical bonds on the surface of the workpiece, chemical agent(s) in the slurry will attract certain atoms from the workpiece surface, thereby removing part of the surface material (e.g., chemical leaching). Consequently, microscopic regions are selectively removed from the surface being polished, thereby enhancing the planarity of the polished workpiece surface. Planarization, however, need only be performed when necessary to prevent the peak-to-valley differential from exceeding the depth of photolithographic focus; or, alternatively, any time a new layer is deposited over a developed circuit layer.

A suitably adapted and effective CMP process may generally be considered as one that provides a high polishing rate which generates a substrate surface that is both finished (e.g., lacks small-scale roughness) and flat (e.g., lacks large-scale topographic differentials). The desired polishing rate, finish and flatness has conventionally been controlled or otherwise modified, for example, by selection of: the pad and slurry combination; the relative speed between the substrate and pad; the force pressing the substrate against the pad; and the method of introducing the slurry to the pad/wafer interface.

An additional consideration in the production of IC's is process/product stability (e.g., quality control). To achieve a high yield (e.g., low defect rate), each developed circuit layer should generally be polished under substantially reproducible conditions so that each IC is substantially indistinguishable from any other IC produced from a different wafer lot. Accordingly, another exemplary embodiment of the present invention includes a system and method for optimization of polishing throughput while providing for improved surface planarity and finish by controlling or otherwise actuating the distribution and chemistry of the polishing slurry at any given time in the polishing cycle in order to permit a higher degree of planarization and uniformity of material removed over substantially the entire surface of a processed workpiece. For example, the disclosed system and method for near-field transform spectroscopy may be employed to analyze the composition of any in situ slurry chemistry and/or slurry chemistry waste in order to monitor the progress of a chemical polishing process. Detection of a concentration and/or chemical activity of a particular component may be used to actuate certain polishing process steps, such as, for example: elimination of waste slurry; introduction of fresh slurry; modification of the chemical composition of the slurry; discontinuation of a first polishing mode and engagement of a second polishing mode; distribution of polishing slurry components to predetermined and/or user-selectable regions of the polishing interface; termination of the polishing process and any other chemical polishing process steps now known or hereafter derived or otherwise described in the polishing art.

Various exemplary implementations of the present invention may be applied to any polishing process utilizing chemically reactive slurry polishing agents. Certain representative implementations may include, for example, the polishing and/or planarization of: semiconductor wafers; integrated circuit wafers; integrated circuit dies; magnetic data storage media, including computer hard drives, floppy drives, and other magnetic mass storage media; optical data storage media including CD-ROM's, DVD's and other optical mass storage media; optical waveguides; interferometric components; electromagnetic detectors and any other object having a surface requiring a high degree of planarity. As used herein, the terms "planarity" and "even surface", or any variation thereof, are intended to denote anything that is currently susceptible to being characterized as having: (1) reduced small-scale surface defects; and (2) minimal large-scale topographic differentials, or anything that may hereafter lend itself to the same or similar characterization. The same shall properly be regarded as within the scope and ambit of the present invention. Skilled artisans will also appreciate that various principles may be employed to ascertain and/or realize any number of other benefits associated with near-field transform characterization of polishing slurry chemistry in the planarization of a workpiece surface, including, but not limited to, the improvement of product yield.

Representative Scope of Exemplary Embodiments

The present invention may be described herein in terms of functional block components, timing charts and various processing steps. It should be appreciated that such functional blocks may be realized by any number of hardware and/or software components configured to perform the specified functions. For example, the present invention may employ various integrated circuit components (i.e., memory elements, processing elements, logic elements, database elements, matchable data structures, and the like) which may carry out a variety of functions under the control of one or more microprocessors or other control devices. Similarly, the software elements of the present invention may be implemented with any programming or scripting language such as, for example: C; C++; Java; Fortran; HPFortran; Pascal; BASIC; Visual BASIC; VBScript; COBOL; LISP; assembler; PERL; eXtensible Markup Language (e.g., XML); Dynamic Hypertext Markup Language (e.g., DHTML); etc. or any other programming or scripting language or combination of programming or scripting languages now known or hereafter derived in the art, with the various algorithms being implemented with any combination of data structures, objects, processes, routines or other programming elements. Further, it should be noted that the present invention may employ any number of conventional techniques for data transmission, signal acquisition, data processing, network control, and the like. Still further, the invention may optionally employ client and/or server and/or client/server network architecture that may further optionally comprise data and/or data-traffic security such as, for example, encryption or any other data and/or data-traffic security protocol now known or hereafter derived in the art.

It will be appreciated by skilled artisans that the particular implementations shown and described herein are illustrative of the invention and its best mode and are not intended to otherwise limit the scope of the present invention in any way. Indeed, for the sake of brevity, conventional signal acquisition, data traffic, data processing and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships and/ or physical connections may be present in a practical system; the same shall be considered within the scope of the present invention.

It will be further appreciated that many applications of the present invention may be formulated with respect to signal acquisition, data traffic, data processing and the like. One skilled in the art will appreciate that a data network may be employed wherein the network may comprise any system for exchanging data, such as, for example: the Internet; an intranet; an extranet; a WAN; a LAN; a PAN: a BAN; a WWAN; a WLAN; a WPAN; a WBAN; satellite communications, and/or the like. Users may interact with the system via any input device such as a keyboard, mouse, kiosk, personal digital assistant, handheld computer (i.e., Palm Pilot®), mobile phone, wireless device and/or the like. Similarly, the invention may be used in conjunction with any type of personal computer, network computer, workstation, minicomputer, mainframe, or the like running any operating system such as any version of Windows, Windows XP, Windows Whistler, Windows ME, Windows NT, Windows 2000, Windows 98, Windows 95, MacOS, OS/2, BeOS, Linux, UNIX, or any operating system now known or hereafter derived by those skilled in the art. Moreover, network data traffic may be readily implemented with various communications protocols such as: TCP/IP; IPX; Appletalk; IP-6; NetBIOS; OSI or any number of existing or future protocols.

Computing or processing units may be connected with each other via a data communications network. The network may be a public network assumed to be insecure and open to eavesdroppers. In one exemplary implementation, the network may be embodied as the Internet wherein computers may or may not be connected to the internet at all times. Specific information related to data traffic protocols, standards, and application software utilized in connection with the Internet may be obtained, for example, from Dilip Naik, *Internet Standards and Protocols,* 1988; various authors, *Java 2 Complete,* 1999; Deborah and Eric Ray, *Mastering HMTL* 4.0, 1997; Loshin, *TCP/IP Clearly Explained,* 1997. A variety of conventional communications media and protocols may be used for data links, such as, for example, a connection to an Internet Service Provider (ISP) over the local loop as is typically used in connection with standard modem communication, cable modem, Dish networks, ISDN, Digital Subscriber Line (DSL), Bluetooth® communications appliances or various data communication methods including wireless data communication methods. Such communication methods are well known in the art, and are covered in a variety of standard texts. See, for example, Gilbert Held, *Understanding Data Communications,* 1996.

As will be further appreciated by skilled artisans, the present invention may be embodied as a method, a system, a device, and/or a computer program product. Accordingly, the present invention may take the form of an entirely software embodiment, an entirely hardware embodiment, or an embodiment combining aspects of both software and hardware. Furthermore, the present invention may take the form of a computer program product on a computer-readable storage medium having computer-readable program code means embodied in the storage medium. Any suitable computer-readable storage medium may be utilized, including hard disks, CD-ROM, optical storage media, magnetic storage media, and/or the like.

Data communications may be accomplished through any suitable communication means, such as, for example, a telephone network, Intranet, Internet, point of interaction device (personal digital assistant, mobile phone, kiosk, etc.), online communications, off-line communications, wireless communications, and/or the like. One skilled in the art will also appreciate that, for security reasons, any databases, systems, or components of the present invention may consist of any combination of databases or components at a single location or at multiple locations, wherein each database or system includes any of various suitable security features, such as firewalls, access codes, encryption, de-encryption, compression, decompression, and/or the like.

The present invention is described herein with reference to block diagrams and timing chart illustrations of methods, devices (e.g., systems) and/or computer program products according to various exemplary aspects of the invention. It will be understood that each functional block of the block diagrams and timing chart illustrations, and combinations of functional blocks in the block diagrams and timing chart illustrations may be controlled or otherwise actuated by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

Computer program instructions may also be stored in a computer-readable memory that may be adapted to direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and timing chart illustrations support combinations of means for performing the specified functions, combinations of steps for performing the specified functions, and program instruction means for performing the specified functions. It will also be understood that each functional block of the block diagrams and timing chart illustrations, and combinations of functional blocks in the block diagrams and timing chart illustrations, may be implemented by either special purpose hardware-based computer systems which perform the specified functions or steps, or suitable combinations of special purpose hardware and computer instructions.

In the foregoing specification, the invention has been described with reference to specific exemplary embodiments; however, it will be appreciated that various modifications and changes may be made without departing from the scope of the present invention as set forth in the claims below. The specification and figures are to be regarded in an illustrative manner, rather than a restrictive one and all such modifications are intended to be included within the scope of the present invention. Accordingly, the scope of the invention should be determined by the claims appended hereto and their legal equivalents rather than by merely the examples described above. For example, the steps recited in any method or process claims may be executed in any order and are not limited to the specific order presented in the claims. Additionally, the components and/or elements recited in any apparatus claims may be assembled or otherwise operationally configured in a variety of permutations to produce substantially the same result as the present invention and are accordingly not limited to the specific configuration recited in the claims.

Benefits, other advantages and solutions to problems have been described above with regard to particular embodiments; however, any benefit, advantage, solution to problems or any element that may cause any particular benefit, advantage or solution to occur or to become more pronounced are not to be construed as critical, required or essential features or components of any or all the claims.

As used herein, the terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present invention, in addition to those not specifically recited, may be varied or otherwise particularly adapted by those skilled in the art to specific environments, manufacturing specifications, design parameters or other operating requirements without departing from the general principles of the same.

What is claimed is:

1. A method for detecting at least one component in a sample, the method comprising:

providing at least one evanescent near-field region formed by at least an array of apertures and a source of radiation, said apertures comprising dimensions effectively below the diffraction limit of said source of radiation;

providing at least one sample flow-path in effective proximity to said near-field region, said flow-path suitably adapted for moving at least one component of said sample substantially along said at least an array of apertures;

providing a detector in effective proximity to said sample flow-path;

detecting the at least one component in the sample; and providing a processor for processing near-field, time-domain signal input from said detector to produce frequency-domain output by operation of a Fourier transformation (FT).

2. The method of claim 1, wherein said detected component comprises at least one of a molecular reporter, a biomolecule, a biomolecular reporter, a luminescence tag, a fluorescence tag, a phosphorescence tag, a chemiluminescence tag, a magnetic tag, a magnetization tag, a radioactive tag, a nuclear spin-state tag, a chemical reagent, a chemical precursor and a nanoprobe.

3. The method of claim 1, wherein said provision of said source radiation is at least one of monochromatic radiation, polychromatic radiation, polarized radiation, circularly-polarized radiation, coherent radiation, incoherent radiation, a particle beam, visible light, ultraviolet light, infrared light, radio waves microwaves, x-rays and gamma rays.

4. The method of claim 1, wherein said sample flow-path comprises at least one of a fluidic channel, a micro-fluidic channel and a nano-fluidic channel.

5. The method of claim 1, wherein said sample flow-path further comprises a chromatographic field.

6. The method of claim 5, wherein said sample flow-path is suitably adapted to use at least one of a gas, a plasma, a liquid and a super-critical fluid as an eluent.

7. The method of claim 1, wherein said detector comprises at least one of a photomultiplier tube (PMT) detector, an avalanche photo diode (APD) detector, and a charge coupled detector (CCD).

8. The method of claim 1, wherein said processing of said time-domain signal comprises at least one of a Fourier transformation, a Laplace transformation, a Hankel transformation, a Mellin transformation, a Hadamard transformation and a Hubert transformation.

9. The method of claim 1, wherein said signal input comprises at least one of an analyte signal input and an analyte-quenched signal input.

10. The method of claim 1, further comprising the step of monitoring a chemical polishing process.

11. The method of claim 10, further comprising the step of modifying the polishing chemistry of said chemical polishing process in response to at least one of a detected concentration value of at least one detected component and a detected chemical activity of at least one detected component.

12. The method of claim 10, further comprising the step of terminating the chemical polishing process in response to at least one of a detected concentration value of at least one detected component and a detected chemical activity of at least one detected component.

13. A system for detecting at least one component in a sample, the system comprising:
- at least one evanescent near-field region formed by at least an array of apertures and a source of radiation, said apertures comprising dimensions effectively below the diffraction limit of said source of radiation;
- at least one sample flow-path in effective proximity to said near field region said flow-path suitably adapted for moving at least one component of said sample substantially along said at least one array of apertures;
- a detector in effective proximity to said sample flow-path; and
- a processor for processing near-field, time domain signal input from said detector to produce frequency-domain output by operation of Fourier transformation (FT).

14. The system of claim 13, wherein said sample flow-path comprises at least one of a fluidic channel, a micro-fluidic channel and a nano-fluidic channel.

15. The system of claim 13, wherein said sample flow-path further comprises a chromatographic field.

16. The system of claim 15, wherein said sample flow-path is suitably adapted to use at least one of a gas, a plasma, a liquid and a super-critical fluid as an eluent.

17. Tho system of claim 13, wherein said detector comprises at least one of a photomultiplier tube (PMT) detector, an avalanche photodiode (APD) detector, and a charge-coupled detector (CCD).

18. The system of claim 13, wherein said signal input comprises at least one of an analyte signal input and an analyte-quenched signal input.

19. A method for detecting least one component in a sample, the method comprising:
- providing a source of radiation;
- providing an aperture field, said aperture field comprising at least an array of apertures, said apertures comprising dimensions effectively below the diffraction limit of said radiation;
- providing at least one flow-path in effective proximity to said aperture field, said flow-path suitably adapted for moving at least one component of said sample substantially along said aperture field;
- providing a detector in effective proximity to said sample flow-path;
- detecting the at least one component in the sample; and
- providing a processor for processing near-field, time-domain signal input from said detector to produce frequency-domain output by operation of a Fourier transformation (FT).

20. The method of claim 19, wherein said detected component comprises at least one of a molecular reporter, a biomolecule, a biomolecular reporter, a luminescence tag, a fluorescence tag, a phosphorescence tag, a chemiluminescence tag, a magnetic tag, a magnetization tag, a radioactive tag, a nuclear spin-state tag, a chemical reagent, a chemical precursor and a nanoprobe.

21. The method of claim 19, wherein said radiation comprises at least one of monochromatic radiation, polychromatic radiation, polarized radiation, circularly-polarized radiation, coherent radiation, incoherent radiation, a particle beam, visible light, ultraviolet tight, infrared light, radio waves, microwaves, x-rays and gamma rays.

22. The method of claim 19, wherein said sample flow-path comprises at least one of a fluidic channel, a micro-fluidic channel and a nano-fluidic channel.

23. The method of claim 19, wherein said sample flow-path further comprises a chromatographic field.

24. The method of claim 23, wherein said sample flow-path is suitably adapted to use at least one of a gas, a plasma, a liquid and a super-critical fluid as an eluent.

25. The method of claim 19, wherein said detector comprises at least one of a photomultiplier tube (PMT), an avalanche photodiode (APD), and a charge-coupled device (CCD).

26. The method of claim 19, wherein said processing of said time-domain signal comprises at least one at a Fourier transformation, a Laplace transformation, a Hankel transformation, a Mellin transformation, a Hadamard transformation and a Hilbert transformation.

27. The method of claim 19, wherein said signal input comprises at least one of an analyte signal and an analyte-quenched signal.

28. A system for detecting at least one component in a sample, the system comprising:
- a source of radiation;
- an aperture field, said aperture field comprising at least an array of apertures, said apertures comprising dimensions effectively below the diffraction limit of said radiation;
- at least one flow-path in effective proximity to said aperture field, said flow-path suitably adapted for moving at least one component of said sample substantially along said aperture field;
- a detector in effective proximity to said sample flow-path; and
- a processor for processing near-field, time-domain signal input from said detector to produce frequency-domain output by operation of a Fourier transformation (FT).

29. The system of claim 28, wherein said radiation comprises at least one of monochromatic radiation, polychromatic radiation, polarized radiation, circularly-polarized radiation, coherent radiation, incoherent radiation, a particle beam, visible light, ultraviolet light, infrared light, radio waves, microwaves, x-rays and gamma rays.

30. The system of claim 28, wherein said sample flow-path comprises at least one of a fluidic channel, a micro-fluidic channel and a nano-fluidic channel.

31. The system of claim 28, wherein said sample flow-path further comprises a chromatographic field.

32. The system of claim 31, wherein said sample flow-path is suitably adapted to use at least one of a gas, a plasma, a fluid and a super-critical fluid as an eluent.

33. The system of claim 28, wherein said detector comprises at least one of a photomultiplier tube (PMT), an avalanche photodiode (APD), and a charge-coupled device (CCD).

34. The system of claim 28, wherein said signal input comprises at least one of an analyte signal and an analyte-quenched signal.

35. A method for detecting at least one component in a sample, the method comprising:

exposing a first side of an aperture field to radiation, said aperture field defined by at least an array of apertures, said apertures having dimensions effectively below the diffraction limit of said radiation;

flowing said sample through a flow-path, said sample flow-path oriented substantially along said aperture field, said sample flow-path in effective near-field proximity to a second side of said aperture field, said sample flow-path in effective proximity to a detector;

interrogating at least one property of said sample; and processing near-field, time-domain signal input obtained from said detector to produce frequency-domain output by operation of a Fourier transformation (FT).

36. The method of claim 35, wherein said property comprises at least one of a quantum state transition, a meta-stable atomic state transition, a nuclear spin-state transition, an electronic spin-state transition, an electronic state transition, a rotational state transition, a vibrational state transition, a biomolecular interaction, a kinetic rate constant, a chromatographic mobility, an index of refraction and magnetic susceptibility.

37. The method of claim 35, wherein said processing of said time-domain signals comprises at least one of a Fourier transformation, a Laplace transformation, a Hankel transformation, a Mellin transformation, a Hadamard transformation and a Hilbert transformation.

38. A near-field system for detecting a biomolecule in a multi-component sample, said system comprising:

a source of electromagnetic radiation;

an array of near-field apertures;

a microchannel sample flow-path;

a detector for collecting a near-field signal generated by the motion of said biomolecule; and a processor for processing near-field, time-domain signal input to produce frequency-domain output by operation of a Fourier transformation (FT).

39. A near-field method for detecting a biomolecule in a multi-component sample, said method comprising:

providing a source of electromagnetic radiation;

providing an array of near-field apertures;

providing a microchannel sample flow-path;

providing a detector for collecting a near-field signal generated by the motion of said biomolecule;

detecting the biomolecule in the multi-component sample; and providing a processor for processing near-field, time-domain signal input to produce frequency-domain output by operation of a Fourier transformation (FT).

40. The method of claim 39, further comprising:

exposing said array of near-field apertures to electromagnetic radiation;

flowing said sample through said microchannel sample flow-path;

interrogating at least one physical property of said sample;

collecting a near-field, time-domain signal generated by the motion of said biomolecule; and processing said time-domain signal input to produce frequency-domain output.

* * * * *

UNITED STATES PATENT AND TRADEMARK OFFICE
CERTIFICATE OF CORRECTION

PATENT NO. : 6,858,436 B2 Page 1 of 1
DATED : February 22, 2005
INVENTOR(S) : Frederic Zenhausern and Chia-Fu Chou It is certified that error appears in the above-identified patent and that said Letters Patent is hereby corrected as shown below:

Column 52,
Line 64, delete "Hubert" and insert -- Hilbert -- therefore.

Signed and Sealed this

Twenty-fourth Day of May, 2005

JON W. DUDAS
*Director of the United States Patent and Trademark Office*